(12) United States Patent
Faust et al.

(10) Patent No.: US 7,850,658 B2
(45) Date of Patent: Dec. 14, 2010

(54) SUBCUTANEOUS INFUSION DEVICE AND METHOD INCLUDING RELEASE FEATURE FOR ADHESIVE PORTION

(75) Inventors: Mark Faust, Lino Lakes, MN (US); Timothy Bresina, Shoreview, MN (US); James Marrs, Arden Hills, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 962 days.

(21) Appl. No.: 10/918,212

(22) Filed: Aug. 13, 2004

(65) Prior Publication Data
US 2005/0113761 A1 May 26, 2005

Related U.S. Application Data

(63) Continuation-in-part of application No. 10/705,736, filed on Nov. 10, 2003, now Pat. No. 7,699,808.

(51) Int. Cl.
*A61M 5/32* (2006.01)
(52) U.S. Cl. .................................... 604/174; 604/180
(58) Field of Classification Search .............. 604/890.1, 604/891.1, 93.01, 164.01, 158, 174–175, 604/180, 288.01, 288.02–288.03
See application file for complete search history.

(56) References Cited

U.S. PATENT DOCUMENTS

| | | | |
|---|---|---|---|
| 3,547,119 A | 12/1970 | Hall et al. | |
| 4,531,937 A | 7/1985 | Yates | |
| 4,563,177 A | 1/1986 | Kamen | |
| 4,755,173 A | * 7/1988 | Konopka et al. | 604/167.02 |
| 4,994,042 A | 2/1991 | Vadher | |
| 5,092,853 A | 3/1992 | Couvertier, II | |
| 5,129,884 A | 7/1992 | Dysarz | |

(Continued)

FOREIGN PATENT DOCUMENTS

DE 299 05 072 U1 9/1999

(Continued)

OTHER PUBLICATIONS

"Technical Information Sheet Product No. 1538L, 3M™ Medical Rayon Woven Tape on Liner," *3M*, 2 pages (© 2003).

(Continued)

*Primary Examiner*—Nicholas D Lucchesi
*Assistant Examiner*—Gerald Landry, II
(74) *Attorney, Agent, or Firm*—Merchant & Gould P.C.

(57) ABSTRACT

An infusion device including a site and a set for delivery of a substance to a patient. The site can include a cannula that is introduced into a subcutaneous layer of skin of the patient. The site is coupled to the skin of a patient by an adhesive portion including a release feature that allows the patient to remove the adhesive portion from the skin. The set can be coupled to the site by, for example, placing the set over the site and moving the set from an unlocked to a locked position. The substance can then be delivered through the set to the site, and from the site into the patient through the cannula. The set can be oriented at multiple rotational orientations with respect to the site, and can be coupled and uncoupled with the site multiple times.

8 Claims, 22 Drawing Sheets

U.S. PATENT DOCUMENTS

| | | |
|---|---|---|
| 5,135,496 A | 8/1992 | Vetter |
| 5,137,516 A | 8/1992 | Rand et al. |
| 5,176,650 A | 1/1993 | Haining |
| 5,176,662 A * | 1/1993 | Bartholomew et al. ...... 604/513 |
| 5,257,980 A | 11/1993 | Van Antwerp et al. |
| 5,522,803 A | 6/1996 | Teissen-Simony |
| 5,545,143 A * | 8/1996 | Fischell ....................... 604/180 |
| 5,573,510 A | 11/1996 | Isaacson |
| 5,575,777 A | 11/1996 | Cover et al. |
| 5,584,813 A | 12/1996 | Livingston et al. |
| 5,591,188 A | 1/1997 | Waisman |
| 5,676,156 A | 10/1997 | Yoon |
| 5,738,641 A * | 4/1998 | Watson et al. .................. 602/43 |
| 5,833,666 A * | 11/1998 | Davis et al. .................. 604/180 |
| 5,848,990 A | 12/1998 | Cirelli et al. |
| 5,851,197 A | 12/1998 | Marano et al. |
| 5,947,931 A | 9/1999 | Bierman |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,056,726 A | 5/2000 | Isaacson |
| 6,077,244 A | 6/2000 | Botich et al. |
| 6,086,575 A | 7/2000 | Mejslov |
| 6,093,172 A | 7/2000 | Funderburk et al. |
| 6,123,690 A | 9/2000 | Mejslov |
| 6,159,181 A | 12/2000 | Crossman et al. |
| 6,191,338 B1 | 2/2001 | Haller |
| 6,293,925 B1 | 9/2001 | Safabash et al. |
| 6,302,866 B1 | 10/2001 | Marggi |
| 6,355,021 B1 | 3/2002 | Nielsen et al. |
| 6,450,992 B1 | 9/2002 | Cassidy, Jr. |
| 6,520,938 B1 | 2/2003 | Funderburk et al. |
| 6,572,586 B1 | 6/2003 | Wojcik |
| 6,579,267 B2 | 6/2003 | Lynch et al. |
| 6,607,509 B2 | 8/2003 | Bobroff et al. |
| 6,685,674 B2 | 2/2004 | Douglas et al. |
| 6,736,797 B1 | 5/2004 | Larsen et al. |
| 6,749,589 B1 | 6/2004 | Douglas et al. |
| 6,926,694 B2 | 8/2005 | Morano-Ford |
| 7,018,344 B2 | 3/2006 | Bressler et al. |
| 7,052,483 B2 | 5/2006 | Wojcik |
| 7,056,302 B2 | 6/2006 | Douglas |
| 7,129,389 B1 * | 10/2006 | Watson ......................... 602/48 |
| 2001/0053889 A1 | 12/2001 | Marggi et al. |
| 2002/0010423 A1 * | 1/2002 | Gross et al. .................. 604/143 |
| 2002/0045867 A1 | 4/2002 | Nielsen et al. |
| 2002/0077599 A1 | 6/2002 | Wojcik |
| 2002/0082543 A1 * | 6/2002 | Park et al. ....................... 604/21 |
| 2002/0123740 A1 * | 9/2002 | Flaherty et al. ........... 604/890.1 |
| 2002/0161332 A1 | 10/2002 | Ramey |
| 2002/0173769 A1 | 11/2002 | Gray et al. |
| 2003/0014018 A1 | 1/2003 | Giambattista et al. |
| 2003/0060781 A1 | 3/2003 | Mogensen et al. |
| 2003/0060798 A1 * | 3/2003 | Fischer et al. ................ 604/501 |
| 2003/0109829 A1 | 6/2003 | Mogensen et al. |
| 2003/0125669 A1 | 7/2003 | Safabash et al. |
| 2003/0130619 A1 | 7/2003 | Safabash et al. |
| 2003/0158520 A1 | 8/2003 | Safabash et al. |
| 2003/0199823 A1 | 10/2003 | Bobroff et al. |
| 2003/0225373 A1 | 12/2003 | Bobroff et al. |
| 2003/0225374 A1 | 12/2003 | Mathiasen |
| 2003/0236498 A1 * | 12/2003 | Gross et al. .................. 604/141 |
| 2004/0002682 A1 | 1/2004 | Kovelman et al. |
| 2004/0116866 A1 * | 6/2004 | Gorman et al. .............. 604/174 |
| 2004/0138612 A1 * | 7/2004 | Shermer et al. ........... 604/93.01 |
| 2004/0143216 A1 | 7/2004 | Douglas et al. |
| 2004/0158207 A1 | 8/2004 | Hunn et al. |
| 2004/0162521 A1 * | 8/2004 | Bengtsson .................. 604/136 |
| 2004/0199123 A1 * | 10/2004 | Nielsen ....................... 604/180 |
| 2004/0204687 A1 | 10/2004 | Mogensen et al. |
| 2004/0260250 A1 | 12/2004 | Harris et al. |
| 2005/0101910 A1 | 5/2005 | Bowman et al. |
| 2005/0101933 A1 | 5/2005 | Marrs et al. |
| 2005/0107743 A1 | 5/2005 | Fangrow, Jr. |
| 2005/0215979 A1 | 9/2005 | Kornerup et al. |
| 2006/0041224 A1 | 2/2006 | Jensen |
| 2006/0173413 A1 | 8/2006 | Fan |
| 2007/0142776 A9 * | 6/2007 | Kovelman et al. ............ 604/136 |

FOREIGN PATENT DOCUMENTS

| | | |
|---|---|---|
| DE | 202 20 543 U1 | 10/2003 |
| EP | 0 290 176 A1 | 11/1988 |
| EP | 0 239 244 B1 | 9/1991 |
| EP | 0 451 040 A1 | 10/1991 |
| EP | 0 615 768 B1 | 12/1999 |
| WO | WO 02/081012 A2 | 10/2002 |

OTHER PUBLICATIONS

International Search Report from Counterpart Foreign Application mailed Dec. 23, 2004.

* cited by examiner

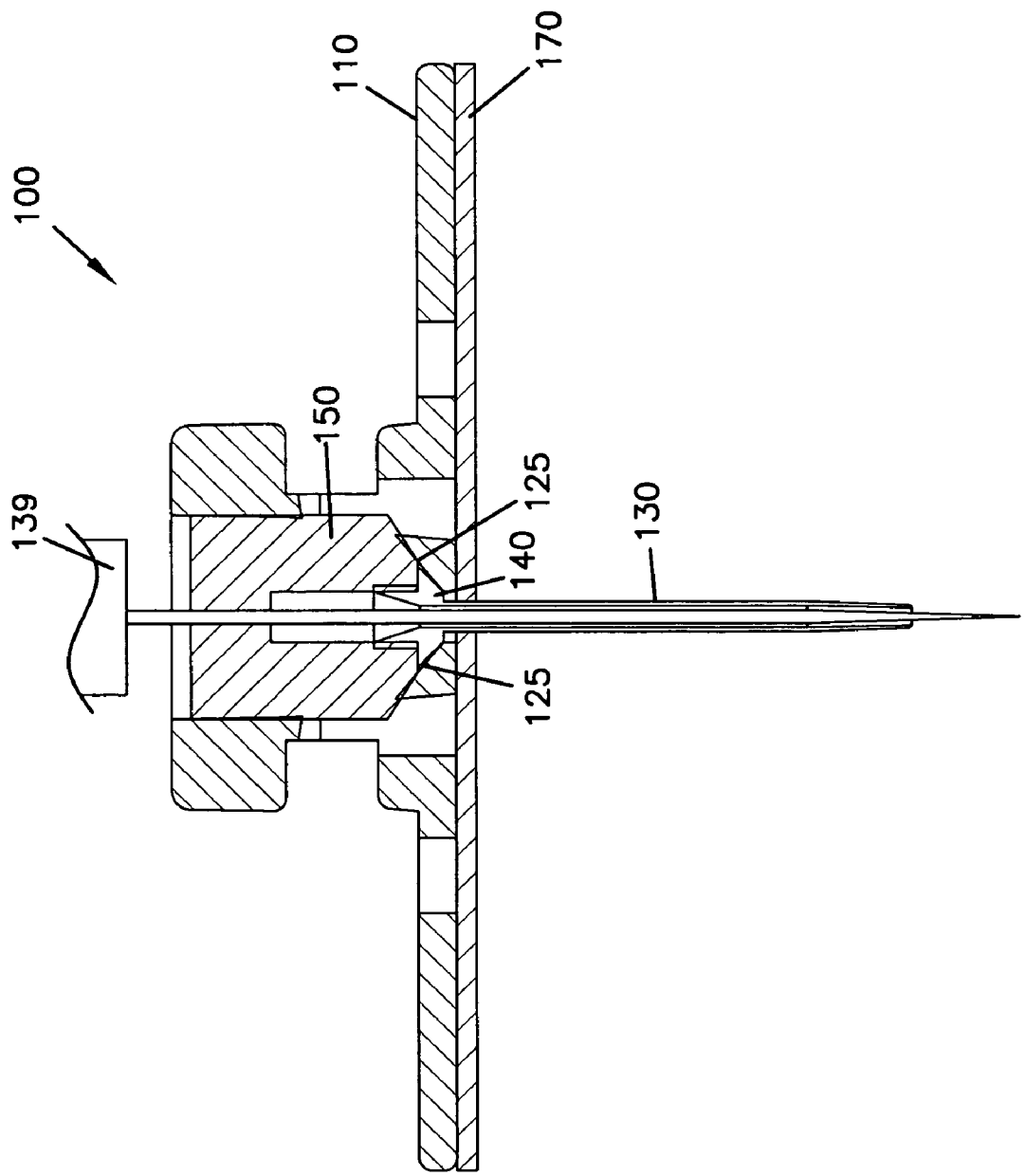

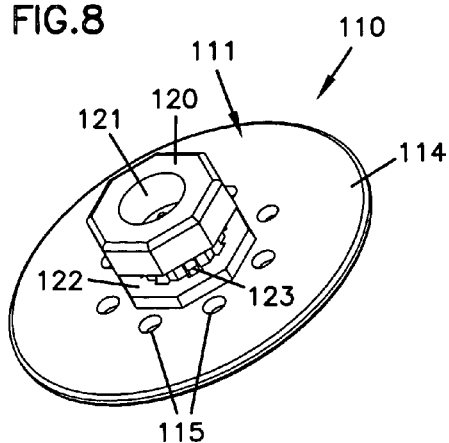
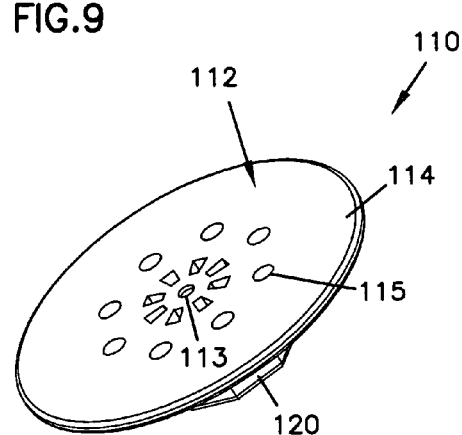
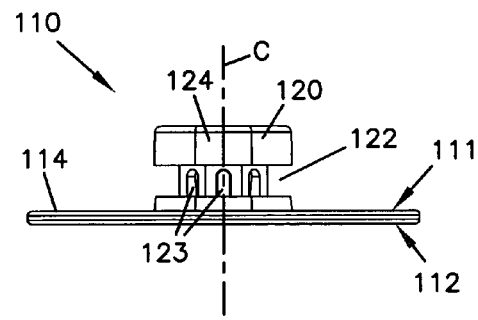
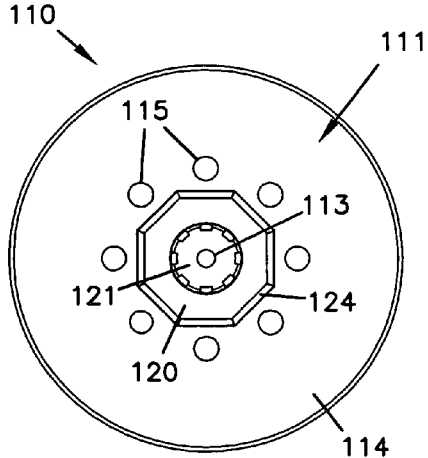

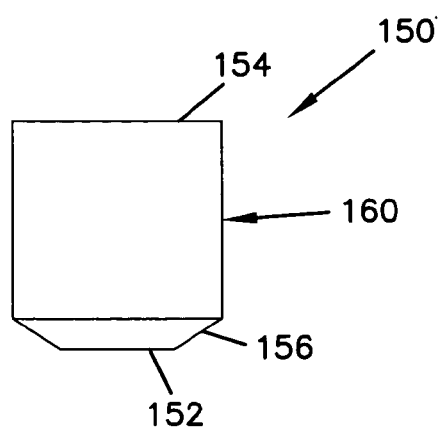
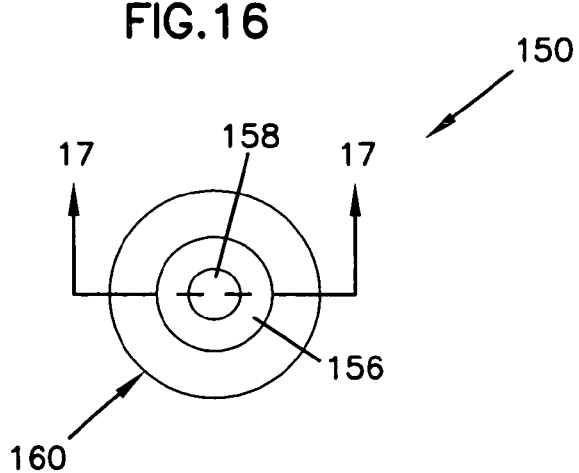
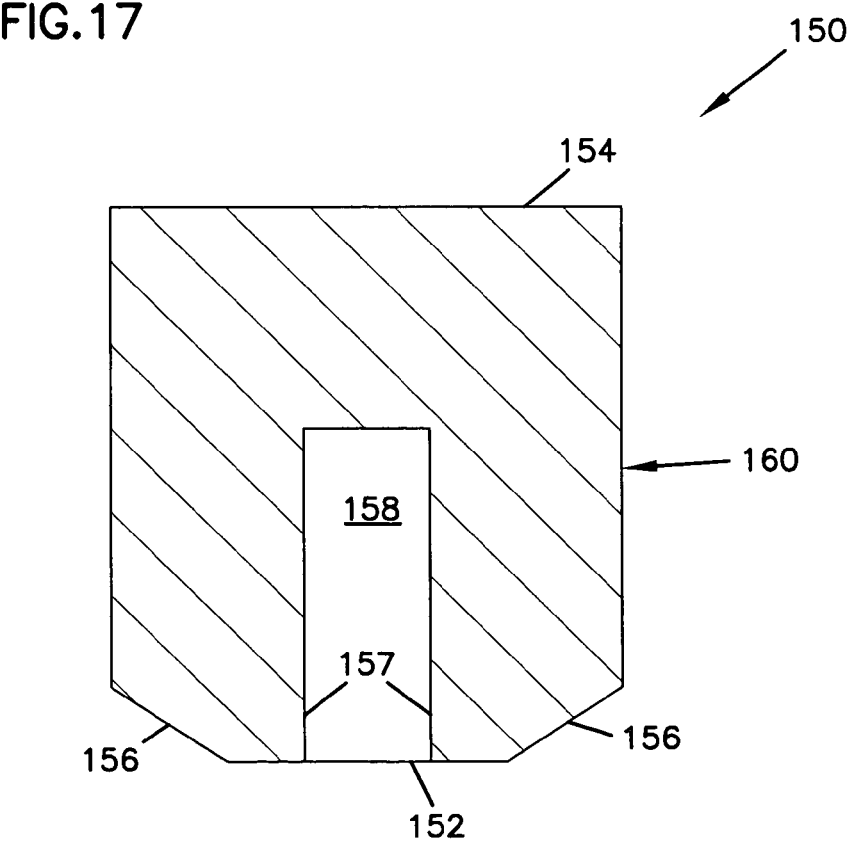

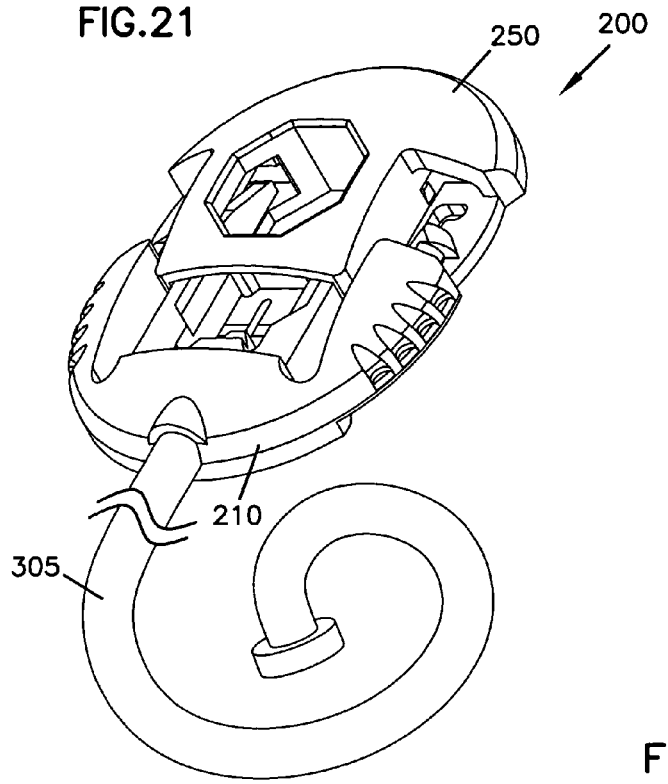
FIG.21
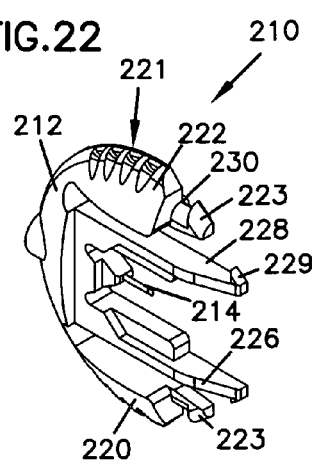
FIG.22
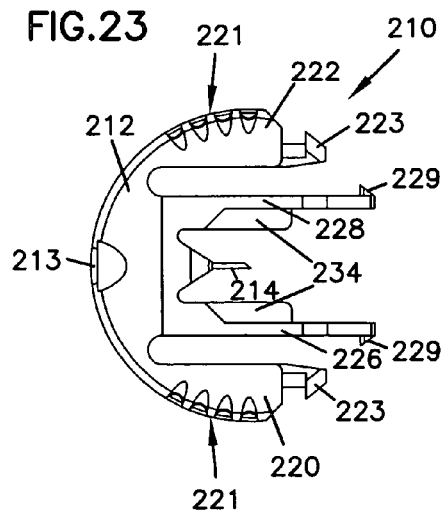
FIG.23
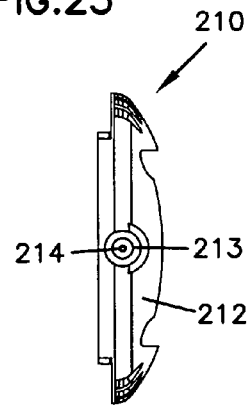
FIG.25
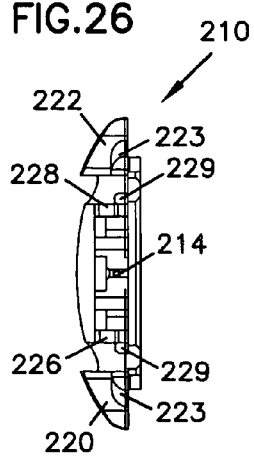
FIG.26
FIG.24

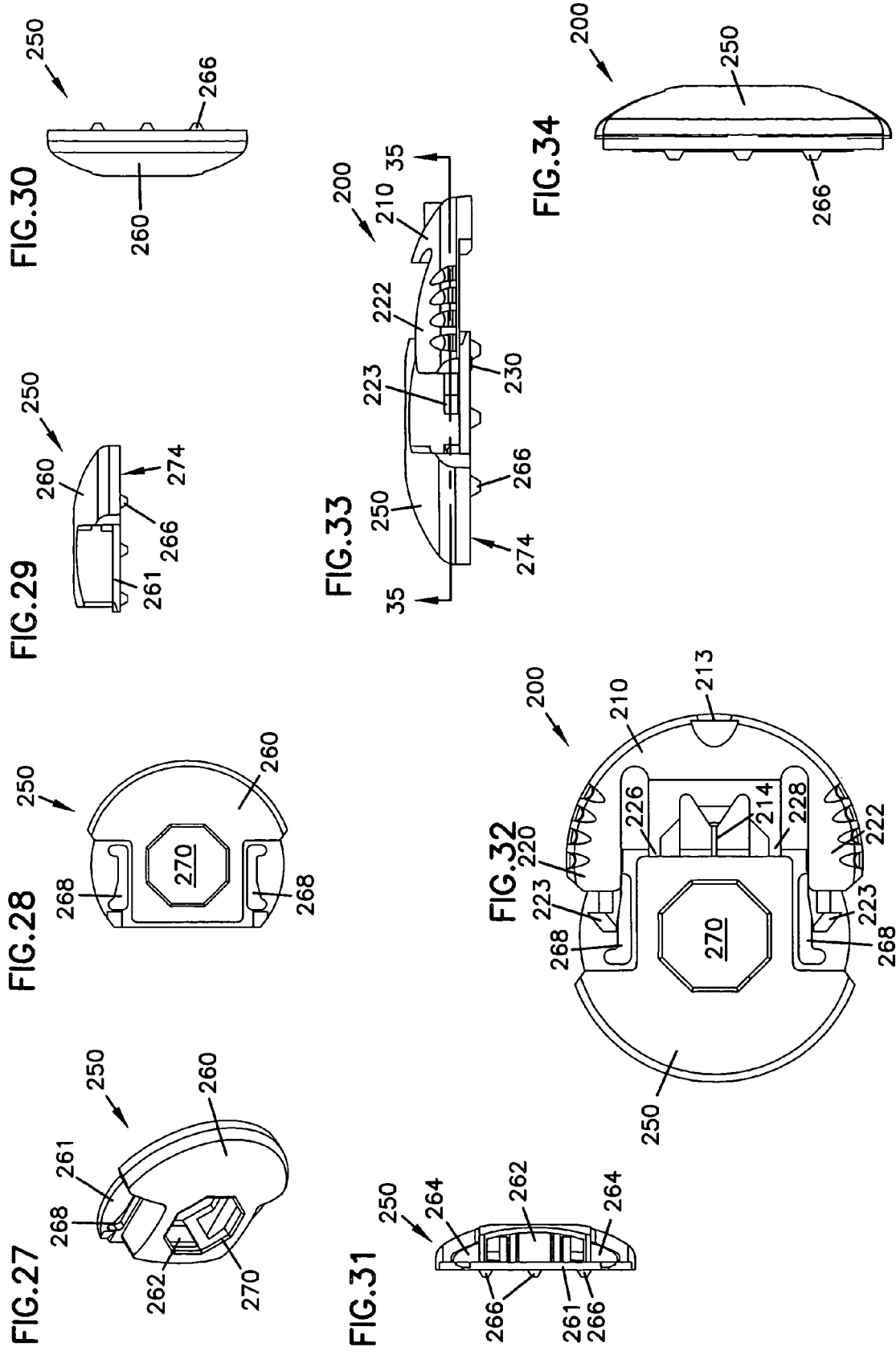

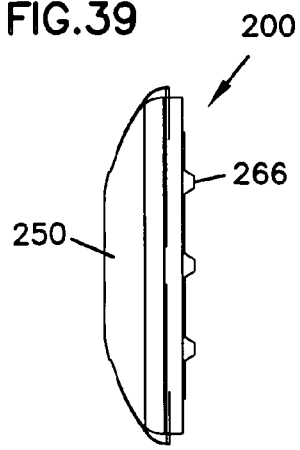
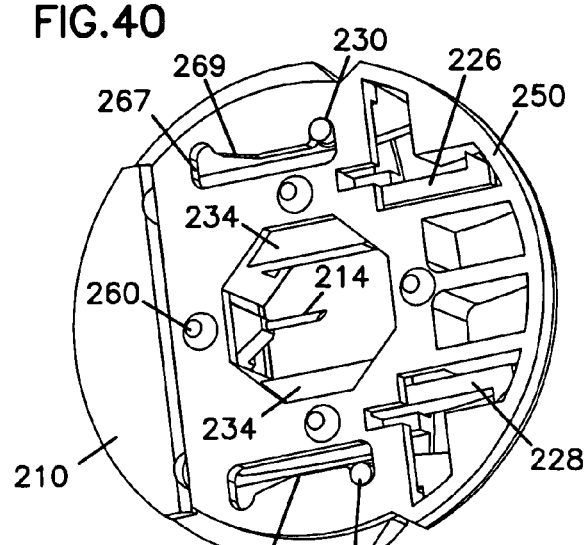
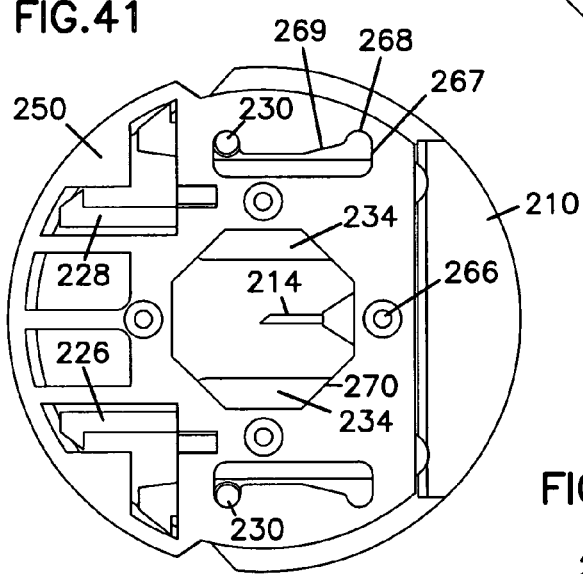
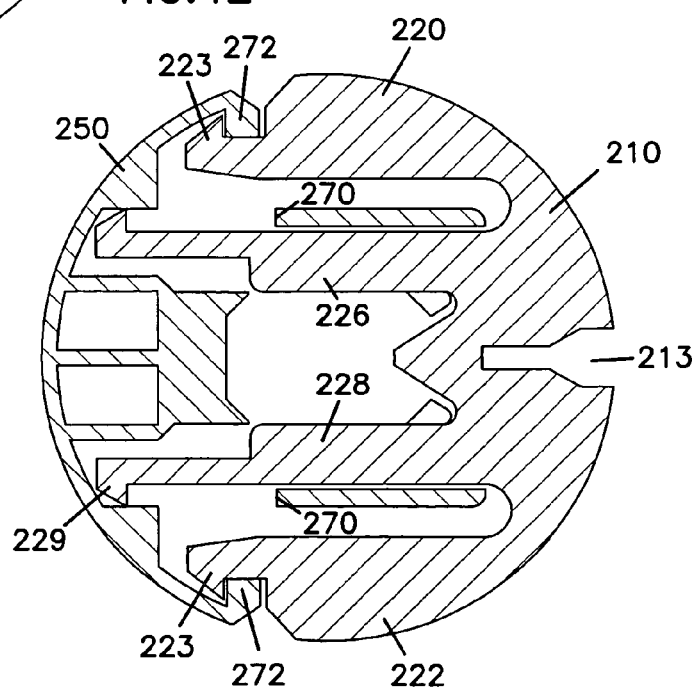

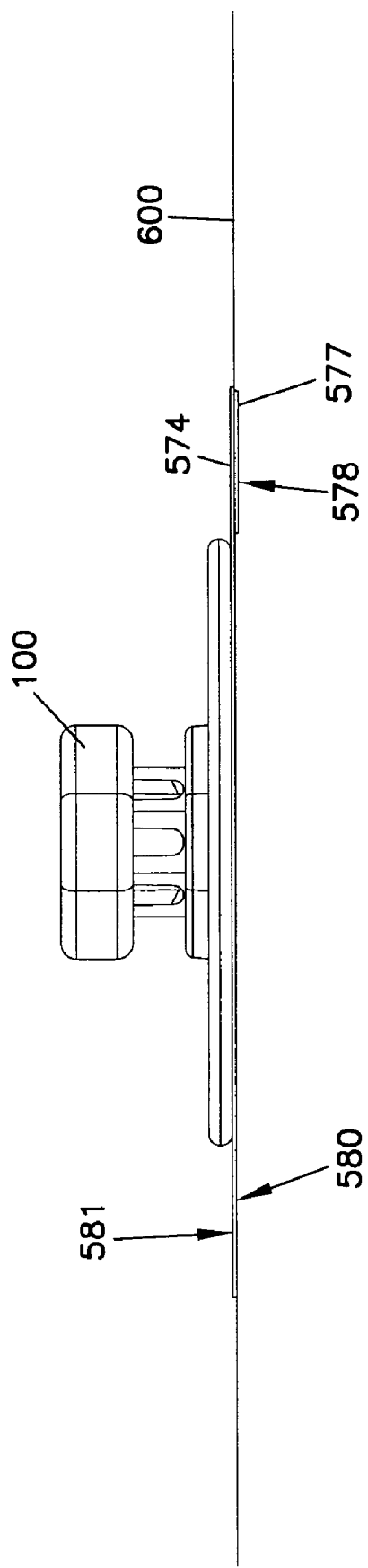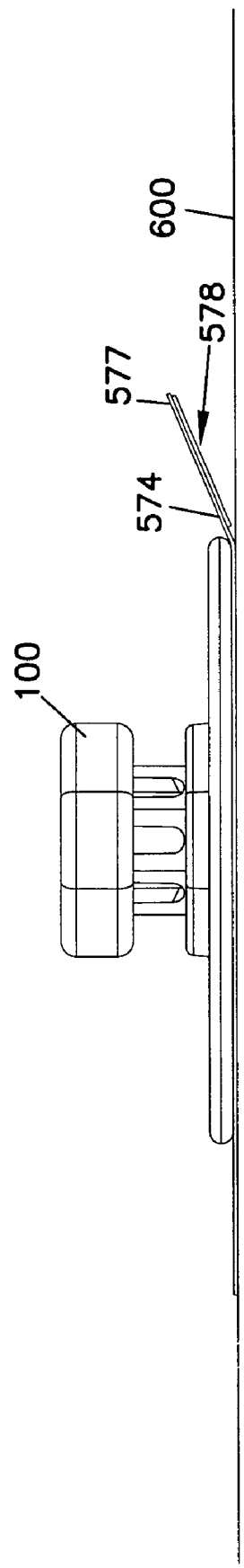

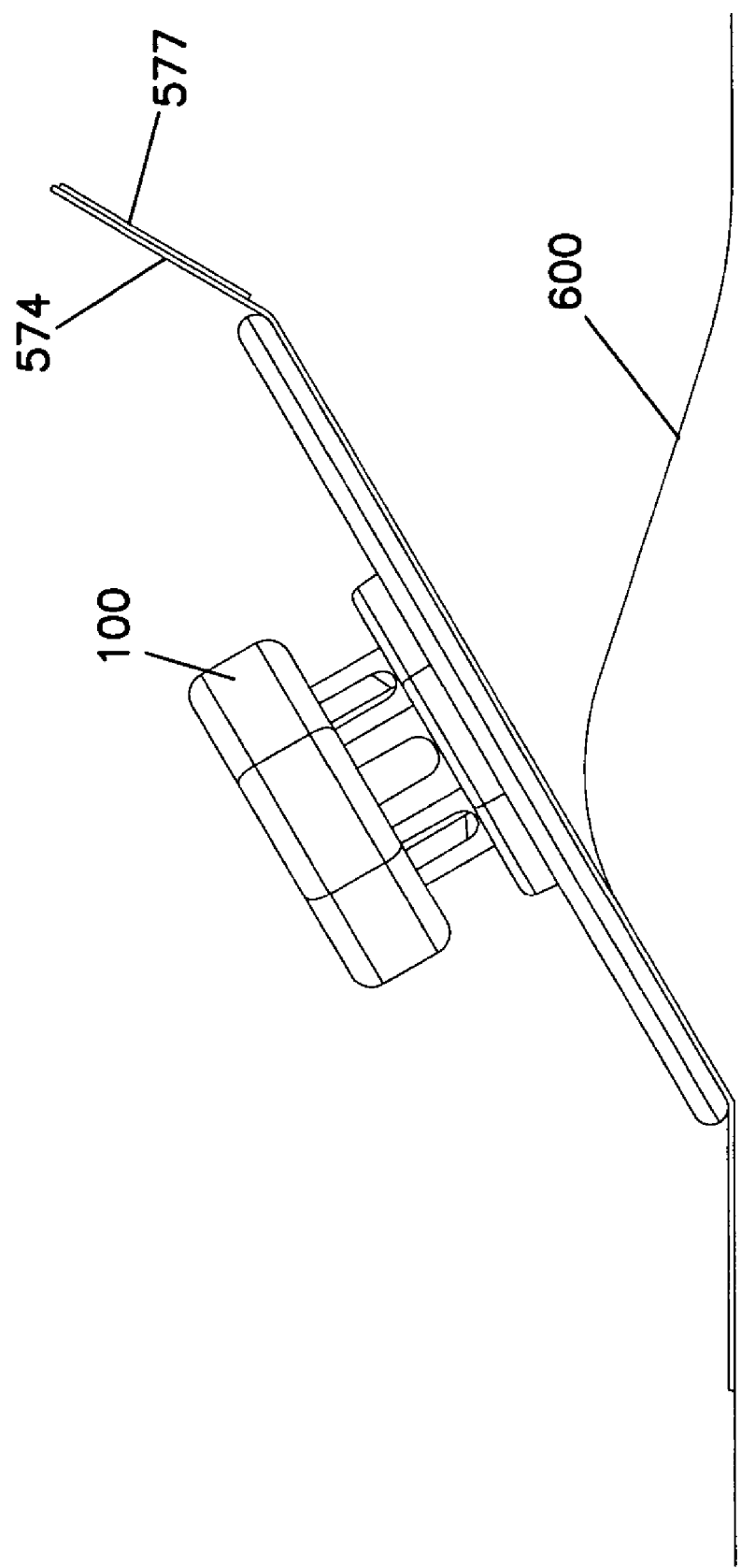

SUBCUTANEOUS INFUSION DEVICE AND METHOD INCLUDING RELEASE FEATURE FOR ADHESIVE PORTION

RELATED APPLICATION

This application is a continuation-in-part of U.S. patent application Ser. No. 10/705,736, entitled "Subcutaneous Infusion Device and Method," and filed on Nov. 10, 2003 now U.S. Pat. No. 7,699,808, the entirety of which is hereby incorporated by reference.

TECHNICAL FIELD

The present invention relates to an infusion device for delivery of a substance to a patient.

BACKGROUND

Infusion devices are used to deliver substances such as medications into the subcutaneous layer of skin of a patient. Typically, an infusion device includes a cannula that is introduced into the skin, as well as a tube extending from the infusion device to, for example, an infusion pump to deliver the substance.

In current designs, it is typically necessary to introduce a cannula of the infusion device into the skin while maintaining the device at a given orientation so that the tubing extends in a direction towards the infusion pump. Further, once the infusion device is placed on the skin, there is typically no way to reorient the device and associated tubing, or to remove the tubing from the body without removing the cannula from the skin of the patient. In addition, the profile of infusion devices can be undesirably high, making placement and concealment of the infusion device difficult and uncomfortable to wear. Also, introduction of the infusion devices into the skin can be complicated and require two hands to accomplish. Further, it can be difficult for patients to remove infusion devices from their skin because the infusion devices can be strongly adhered to the skin and layers carrying the adhesives may not be easily grasped by the patients.

It is therefore desirable to provide new designs for infusion devices used to deliver a substance into the skin of a patient.

SUMMARY

Embodiments made in accordance with the present invention are related to infusion devices for delivery of a substance to a patient.

In one embodiment, an infusion device can include a site and a set. The site can include a cannula that is introduced into a subcutaneous layer of skin of the patient. The set can be coupled to the site by, for example, placing the set over the site and moving the set from an unlocked to a locked position. A substance can then be delivered through the set to the site and from the site into the patient through the cannula.

The set can preferably be oriented at multiple rotational orientations with respect to the site, and can preferably be coupled and uncoupled with the site multiple times.

In some embodiments, the adhesive portion that is used to couple the site to the skin can include a release feature that assists the patient in removing the adhesive portion and accompanying site from the skin.

The above summary of the present invention is not intended to describe each disclosed embodiment or every implementation of the present invention. Figures in the detailed description that follow more particularly exemplify embodiments of the invention. While certain embodiments will be illustrated and described, the invention is not limited to use in such embodiments.

DESCRIPTION OF THE DRAWINGS

FIG. 6A is a cross-sectional view taken along line 6-6 of the site of FIG. 3 including a needle used to insert the site.
FIG. 8 is a top perspective view of a base of the site of FIG. 1.
FIG. 9 is a bottom perspective view of the base of FIG. 8.
FIG. 10 is a side view of the base of FIG. 8.
FIG. 11 is a top view of the base of FIG. 8.
FIG. 15 is a side view of a diaphragm of the site of FIG. 1.
FIG. 16 is an end view of the diaphragm of FIG. 15.
FIG. 17 is a cross-sectional view taken along line 17-17 of the diaphragm of FIG. 16.
FIG. 21 is a top perspective view of an example embodiment of a set in an unlocked position made in accordance with the present invention.
FIG. 22 is a top perspective view of a first member of the set of FIG. 21.
FIG. 23 is a top view of the first member of FIG. 22.
FIG. 24 is a side view of the first member of FIG. 22.
FIG. 25 is an end view of the first member of FIG. 22.
FIG. 26 is another end view of the first member of FIG. 22.
FIG. 27 is a top perspective view of a second member of the set of FIG. 21.
FIG. 28 is a top view of the second member of FIG. 27.
FIG. 29 is a side view of the second member of FIG. 27.
FIG. 30 is an end view of the second member of FIG. 27.
FIG. 31 is another end view of the second member of FIG. 27.
FIG. 32 is a top view of the set of FIG. 21 in an unlocked position.
FIG. 33 is a side view of the set of FIG. 32.
FIG. 34 is an end view of the set of FIG. 32.
FIG. 39 is an end view of the set of FIG. 36.

FIG. 40 is a bottom perspective view of the set of FIG. 36.

FIG. 41 is a bottom view of the set of FIG. 36.

FIG. 42 is a cross-sectional view taken along line 42-42 of the set of FIG. 38 with portions of the set removed for clarity.

FIG. 58 is a side view of an example embodiment of a site including an adhesive portion attached to the skin of a patient.

FIG. 59 is another side view of the site of FIG. 58 with a release feature pulled away from the skin of the patient.

FIG. 60 is another side view of the site of FIG. 59 with the release feature and a portion of the adhesive portion of the site pulled away from the skin of the patient.

DETAILED DESCRIPTION

Figure 1:
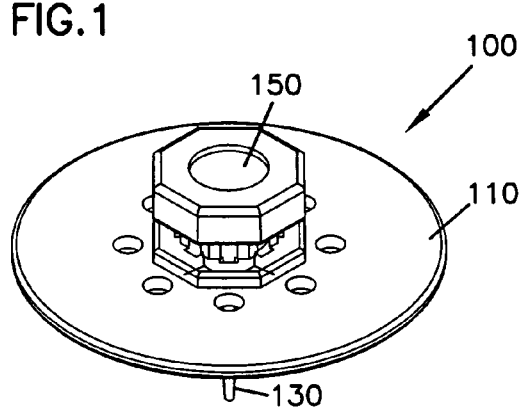
FIG. 1 is a top perspective view of an example embodiment of a site made in accordance with the present invention.
Figure 2:
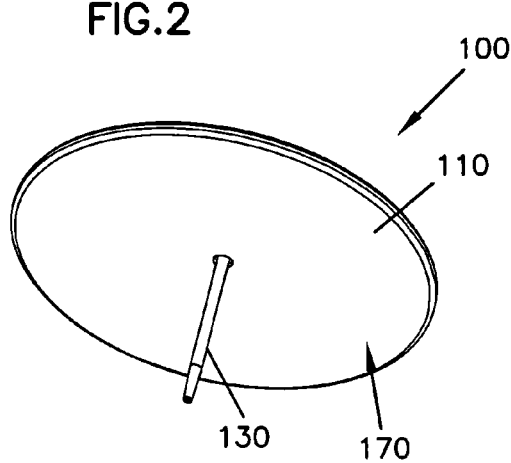
FIG. 2 is a bottom perspective view of the site of FIG. 1.
Figure 3:
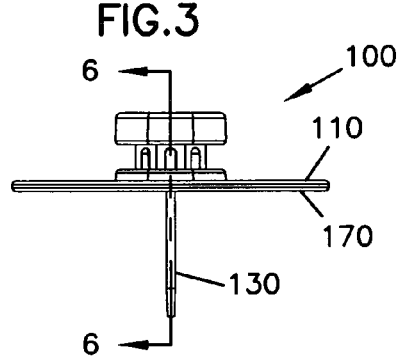
FIG. 3 is a side view of the site of FIG. 1.
Figure 4:
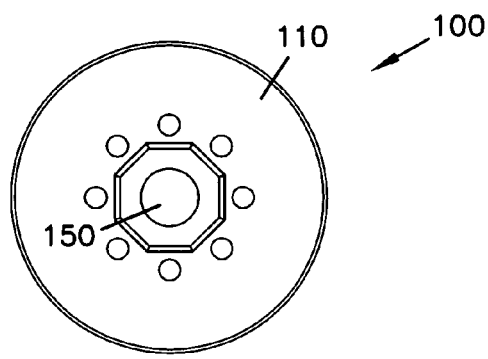
FIG. 4 is a top view of the site of FIG. 1.
Figure 5:
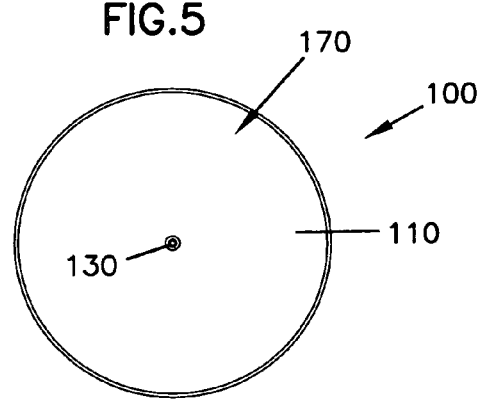
FIG. 5 is a bottom view of the site of FIG. 1.

Embodiments of the present invention relate to infusion devices for delivering a substance into the subcutaneous layer of skin of a patient.

Generally, the example infusion devices disclosed herein include a site with a cannula that is introduced into the subcutaneous layer of the skin of a patient to deliver a substance, as well as a set that can be coupled to the site to deliver the substance to the site.

Referring now to FIGS. 1-7, an example embodiment of a site 100 of an infusion device is depicted in accordance with the present invention. Generally, the site 100 can be used in conjunction with a set (described below) to deliver a substance into a patient.

The site 100 includes a base 110, a cannula 130, a diaphragm 150, and an adhesive portion 170. The cannula 130 of the site 100 can be introduced into the subcutaneous layer of skin of the patient using a needle (e.g., needle 139), as shown in FIG. 6A. The adhesive portion 170 allows the base 110 of the site 100 to be coupled to the skin of the patient. The diaphragm 150 is in fluid communication with the cannula to deliver a substance from the diaphragm 150, through the cannula 130, and into the skin of the patient, as described further below.

Referring now to FIGS. 8-11, the base 110 is shown. The base includes a stand 114 with a top side 111 and a bottom side 112, and forms a central aperture 113 located at a central axis C of the base 110. The stand 114 further forms eight positional slots 115 on the top side 111 positioned radially with respect to the central axis C of the site 110 at regular intervals.

The base 110 also includes a member 120 coupled to the stand 114, the member 120 being positioned about the central aperture 113 of the stand 114 and including eight surfaces 124. In one preferred embodiment, the member 120 is non-cylindrical in shape. For example, in the embodiment shown the member 120 is octagonal in shape, although other shapes can also be used, as noted below. The non-cylindrical shape of member 120 defines different mounting orientations for a set that can be coupled to the site 100.

An interior wall of the member 120 forms a cylindrical cavity 121, and an exterior periphery of the member 120 forms a groove 122 extending about the exterior periphery. In addition, the member 120 forms eight apertures 123 extending from the interior cavity 121 to the groove 122 in the exterior of the member 120.

Figure 12:
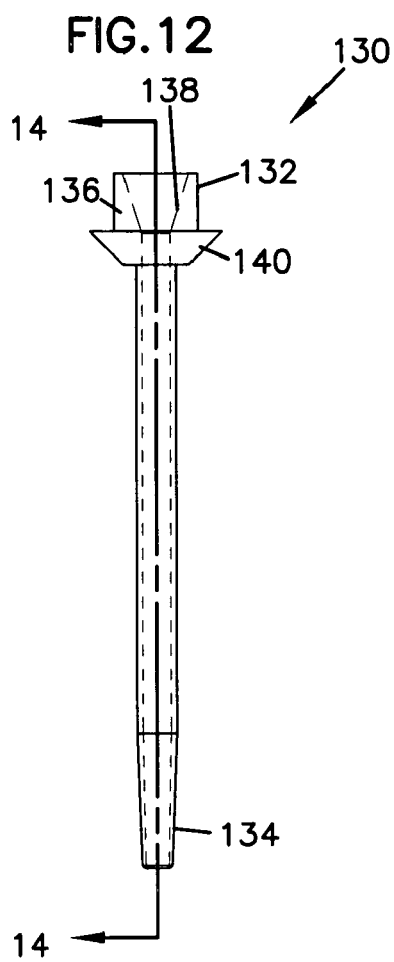
FIG. 12 is a side view of a cannula of the site of FIG. 1.
Figure 13:
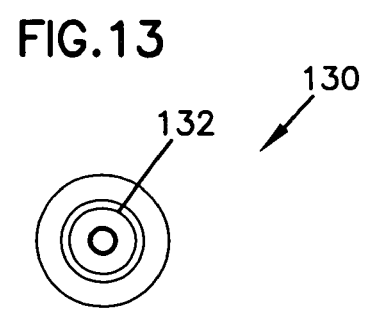
FIG. 13 is an end view of the cannula of FIG. 12.
Figure 14:
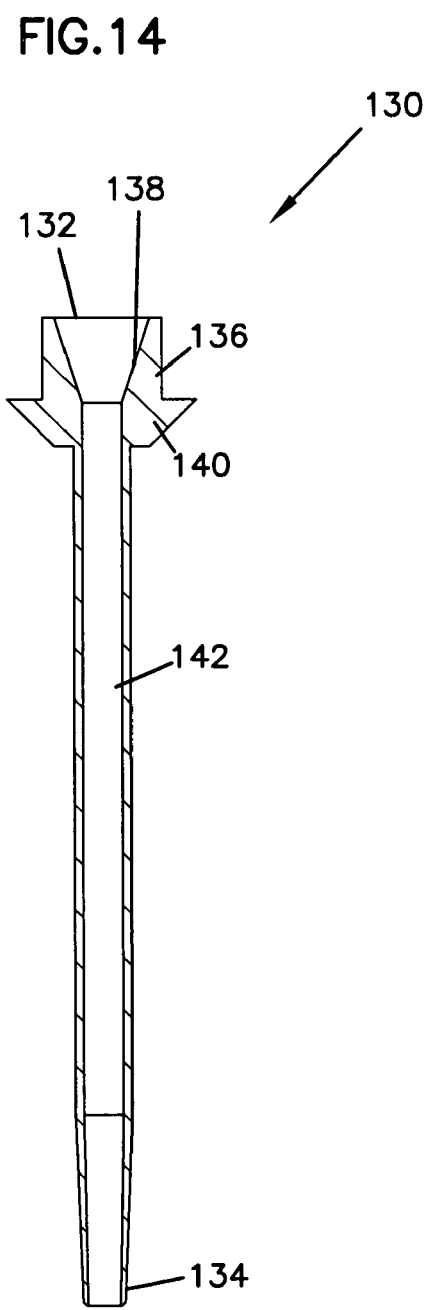
FIG. 14 is cross-sectional view taken along line 14-14 of the cannula of FIG. 12.

Referring now to FIGS. 12-14, the cannula 130 is illustrated. The cannula 130 includes first and second ends 132 and 134. The first end 132 of the cannula 130 includes a flange portion 136 having a tapered bottom side 140, as well as a tapered portion 138 described further below. The cannula 130 also includes a central bore 142 extending from the first end 132 to the second end 134 to allow a substance to be introduced at the first end 132 and delivered out of the second end 134.

The cannula 130 is positioned within the cavity 121 of the base 110 so that the bottom taper 140 of the cannula 130 engages tapered bottom surfaces 125 of the cavity 121 of the member 120, and the second end 134 of the cannula 130 extends through the central aperture 113 of the stand 114 at an approximate right angle to the bottom side 112 of the stand 114. See FIG. 6. Preferably, the bottom taper 140 of the cannula 130 is positioned adjacent to the stand 114 of the base 110.

Preferably the cannula 130 is made of fluorinated ethylene propylene (FEP). Other materials can also be used, such as polytetrafluoroethylene (PTFE), or other suitable plastics.

Referring now to FIGS. 15-17, the diaphragm 150 is shown. Generally, the diaphragm 150 functions as a septum or seal that allows a needle to access an internal portion of the septum to deliver a substance provided, for example, from an infusion device or other similar device to the cannula 130.

Preferably, the diaphragm 150 is generally cylindrical in shape and includes an open bottom end 152 and a closed top end 154. The diaphragm 150 also includes a tapered portion 156 adjacent the bottom end 152, and a central reservoir 158.

Figure 6:
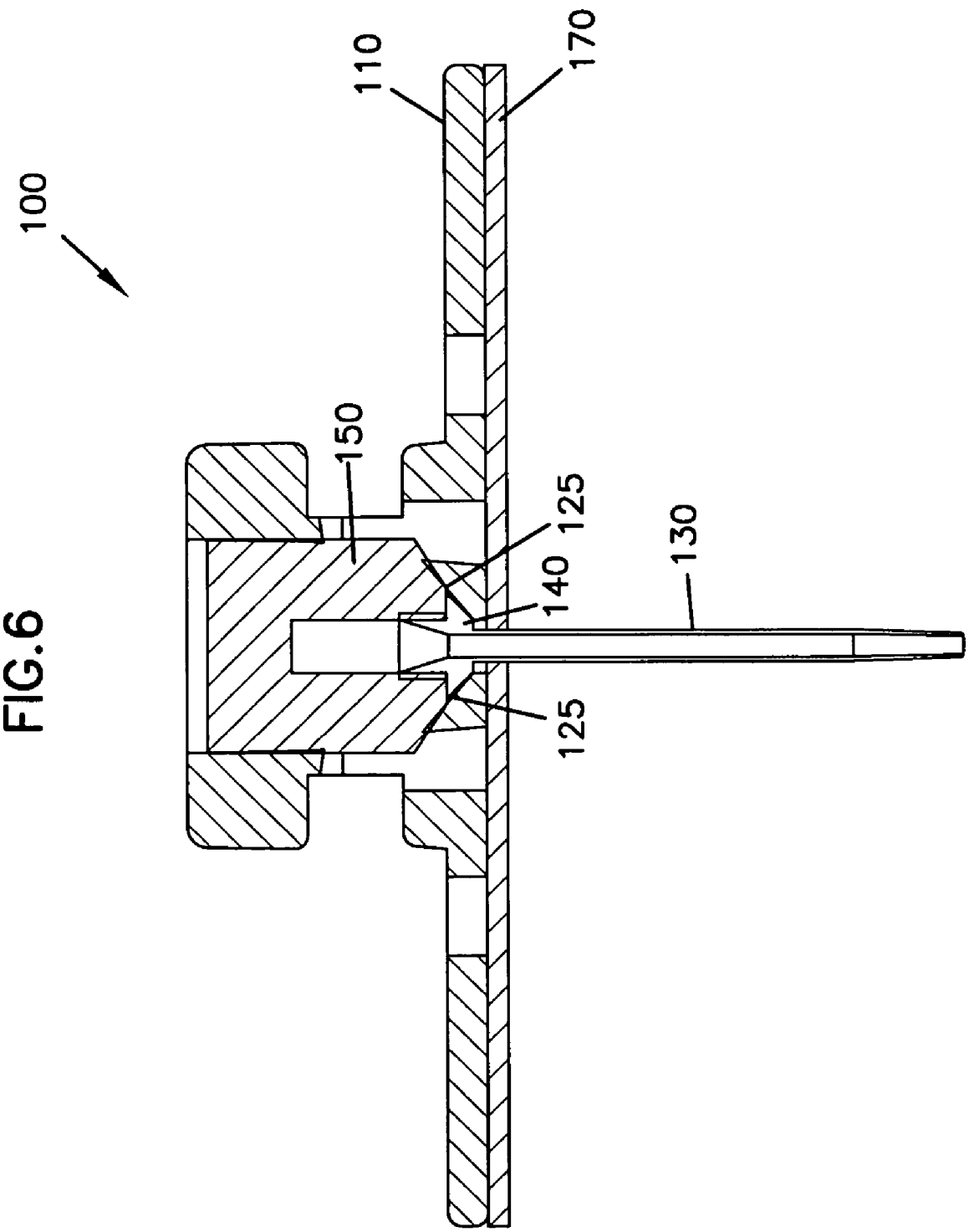
FIG. 6 is a cross-sectional view taken along line 6-6 of the site of FIG. 3.
Figure 7:
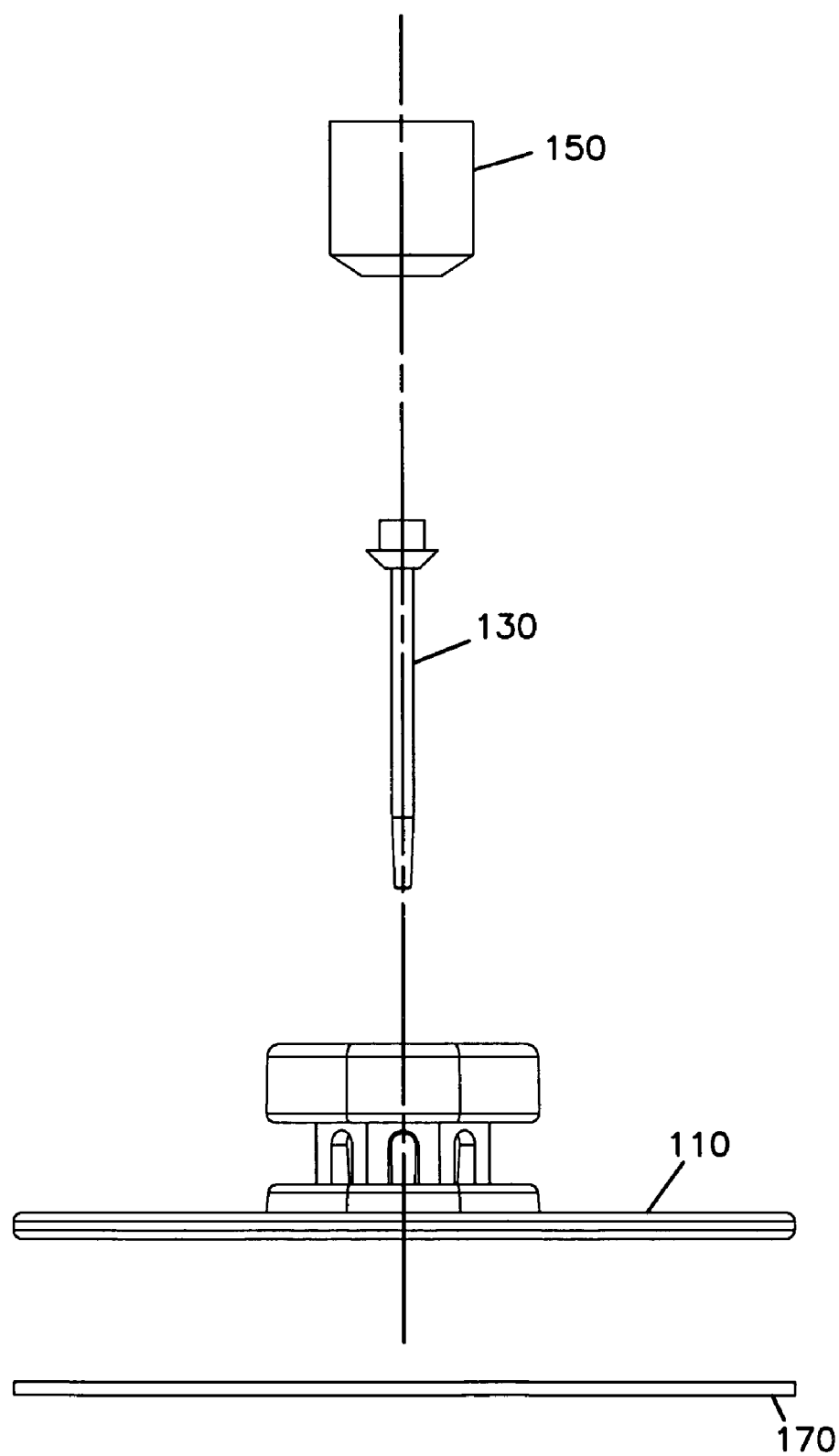
FIG. 7 is an exploded view of the site of FIG. 1.

As shown, for example, in FIGS. 6 and 17, the diaphragm 150 is positioned in the cavity 121 of the member 120 and preferably includes an outer periphery 160 that is sized to frictionally engage the interior cavity wall of the member 120 to retain the diaphragm 150 in the cavity 121. In addition, the tapered portion 156 of the diaphragm 150 is configured to engage the tapered bottom surfaces 125 of the base 110. The bottom end 152 engages the first end 132 of the cannula 130 to provide fluid communication between the reservoir 158 and the bore 142 of the cannula 130.

More specifically, surfaces 157 adjacent to the bottom end 152 of diaphragm 150 preferably are compressed against the first end 132 of the cannula 130 to provide a seal with respect to the cannula 130 so a substance can be delivered from the diaphragm 150, through the cannula 130, and into the patient.

In alternative embodiments, additional structure such as, for example, an O-ring can also be provided between the diaphragm 150 and cannula 130 to provide additional sealing.

In a preferred embodiment, the diaphragm 150 is made of a silicone elastomer. Other materials can also be used, such as ethylene propylene or other suitable elastomeric materials.

As previously noted, preferably the diaphragm 150 is retained in the cavity 121 of the member 120 of the base 110 through the frictional engagement of the outer periphery 160 of the diaphragm 150 with the walls of the cavity 121. In alternative embodiments, a retaining member can be fitted over the open top of the member 120 to further retain the diaphragm 150 in position in the cavity 121. In other embodiments, the diaphragm 150 can be retained in the cavity 121 through compression by other features of the member 120, or the diaphragm 150 can have features that mate with features of the member 120. For example, in one alternative embodiment, the diaphragm 150 can be formed with barbs on the outer periphery 160 positioned and sized to be received within apertures 123 formed in the member 120 to retain the diaphragm 150 in the cavity 120. Other configurations are also possible.

Figure 18:
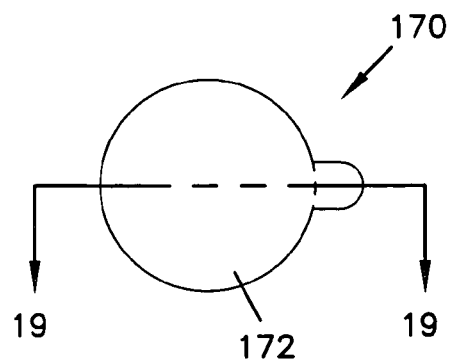
FIG. 18 is a top view of an adhesive portion of the site of FIG. 1.
Figure 19:
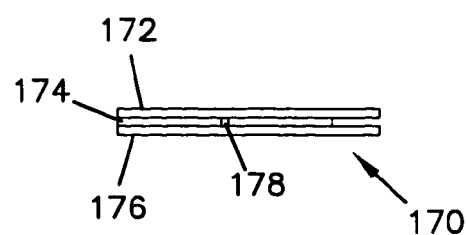
FIG. 19 is a cross-sectional view taken along line 19-19 of the adhesive portion of FIG. 18.
Figure 20:
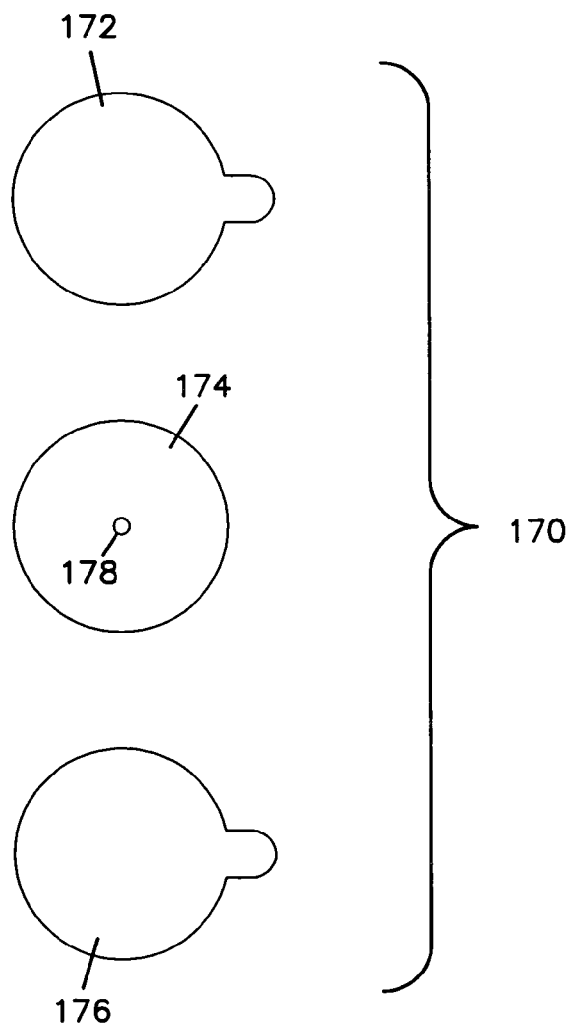
FIG. 20 is an exploded view of the adhesive portion of FIG. 18.

Referring now to FIGS. 18-20, the adhesive portion 170 is shown. The adhesive portion includes liners 172 and 176 sandwiching a layer 174. Preferably, the layer 174 includes an aperture 178 through which the cannula 130 of the site 100 extends, as described below.

The liner 172 can be removed and the layer 174 coupled to the bottom side 112 of the stand 114 of the base 110 using an adhesive. Examples of such adhesives include, without limitation, acrylic adhesive, synthetic rubber-based adhesive, acrylate adhesive, and silicone-based adhesive. In addition, the liner 176 can be removed and an adhesive be provided on a bottom side of the layer 174 to couple the adhesive portion 170 and associated site 100 to another adhesive portion or the skin of the patient, for example.

In a preferred embodiment, layer 174 of the adhesive portion 170 includes films with adhesives thereon, such as and without limitation, 3M™ 1577 tape. Other materials can also be used.

Figure 20A:
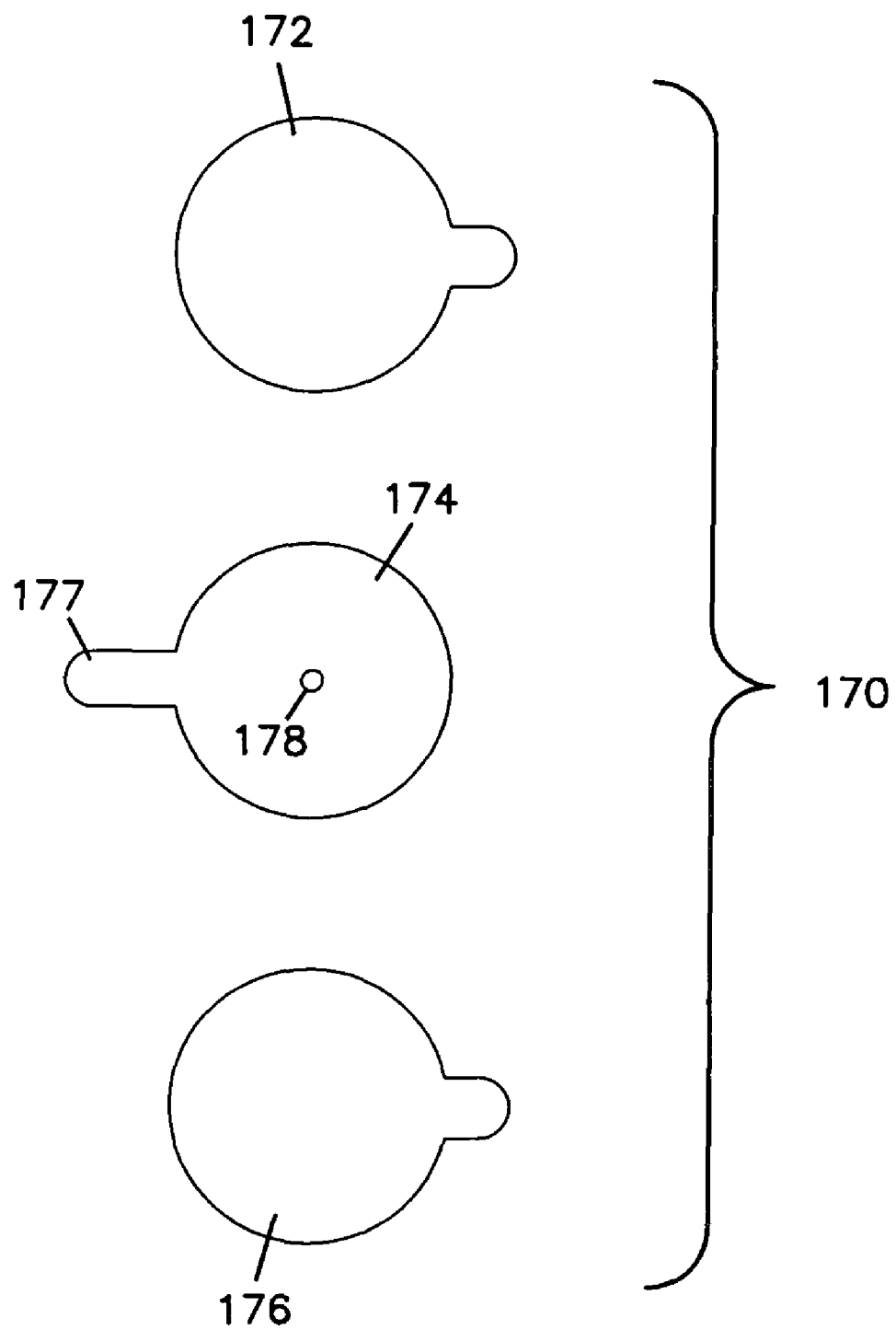
FIG. 20A is an exploded view of another example embodiment of an adhesive portion including an example embodiment of a release feature made in accordance with the present invention.

In an alternative embodiment shown in FIG. 20A, layer 174' can be provided with a release feature such as a tab 177 (or other similar structure) that can assist the patient in removing the layer 174' and associated site 100 from the skin when desired. For example, the tab 177 can extend from an outer periphery of the layer 174' and allow the patient to grasp the tab and thereby peel the layer 174' from the skin to remove the site 100. Other configurations are also possible, as shown in FIGS. 54-61 and described below.

In other alternative embodiments, the adhesive portion 170 can be removed completely, and adhesion between the site 100 and skin of the patient can be provided using film and/or adhesive carried on other structures, such as a device used to insert the site 100 into the body, as described further below.

In other alternative embodiments, the layer 174 can include a foam backing or similar additional material can be added adjacent to the layer 174 to provide supplemental cushioning as the site 100 is inserted into the skin of the patient. Further, in other embodiments the layer 174 can be replaced or supplemented by one or more other layer of other material such as, for example, a Tegaderm™ film manufactured by 3M™ or an IV3000™ film manufactured by Smith & Nephew.

Referring now to FIG. 21, an example embodiment of a set 200 of an infusion device is depicted in accordance with the present invention. As noted generally above and described further below, the set 200 can be used in conjunction with a site (e.g., site 100) to deliver a substance into a patient.

The set 200 generally includes a first member 210 and a second member 250. The first member 210 is slideable relative to the second member 250 into an unlocked position (see, e.g., FIGS. 21 and 32-35) and a locked position (see, e.g., FIGS. 36-42), described further below.

Referring now to FIGS. 22-26, the first member 210 is shown. The first member 210 includes a main body 212, and a port 213 extending through the body 212 and in fluid communication with a hollow needle 214. The port 213 is preferably coupled to a tube (e.g., tube 305 shown in FIG. 21) that can be attached, for example, to an infusion pump for the delivery of a substance to the set 200.

The first member 210 also includes outer arms 220 and 222 with barbs 223 formed on the ends and projections 230 extending below the arms 220. In addition, the first member 210 includes inner arms 226 and 228 with barbs 229. As described further below, the outer arms 220 and 222 can be displaced towards one another when force is applied to surfaces 221.

Referring now to FIGS. 27-31, the second member 250 is shown. The second member 250 includes a main body 260, and a central octagonal aperture 270. The second member 250 also includes opening 262 extending to the central aperture 270, as well as openings 264 positioned on opposite sides of the main body 260. The second member 250 also includes projections 266 formed on a bottom surface 274 of a base 261, as well as slots 268 preferably extending through the base 261 of the main body 260.

Referring now to FIGS. 21 and 32-35, the first and second members 210 and 250 of the set 200 are shown in the unlocked position. The first member 210 is slidingly received by the second member 250 such that inner arms 226 and 228 are accepted into opening 262 of the second member 250. Projections 230 on outer arms 220 and 222 of the first member 210 are received in slots 268 of the second member 250.

Figure 35:
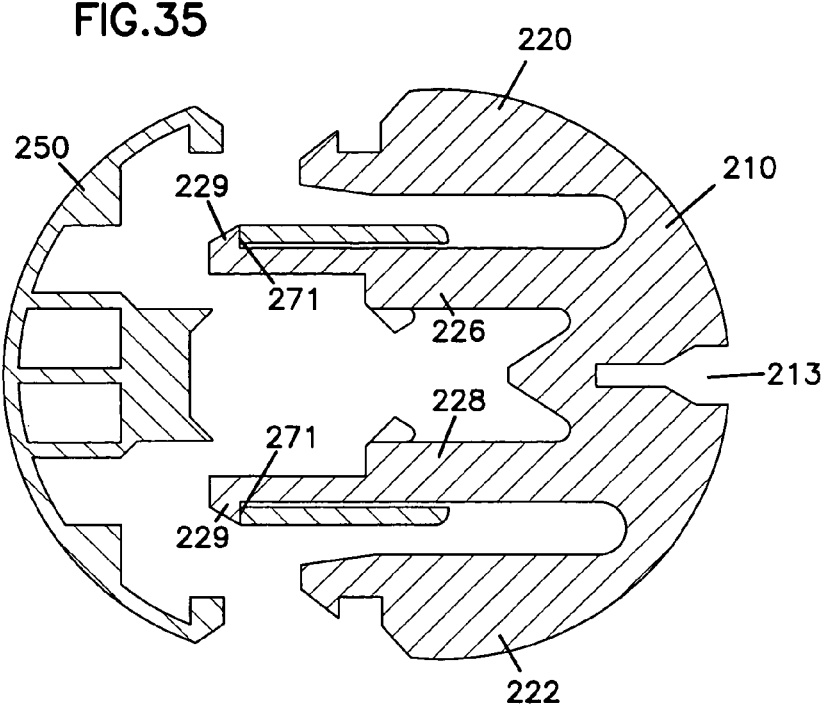
FIG. 35 is a cross-sectional view taken along line 35-35 of the set of FIG. 32 with portions of the set removed for clarity.
Figure 36:
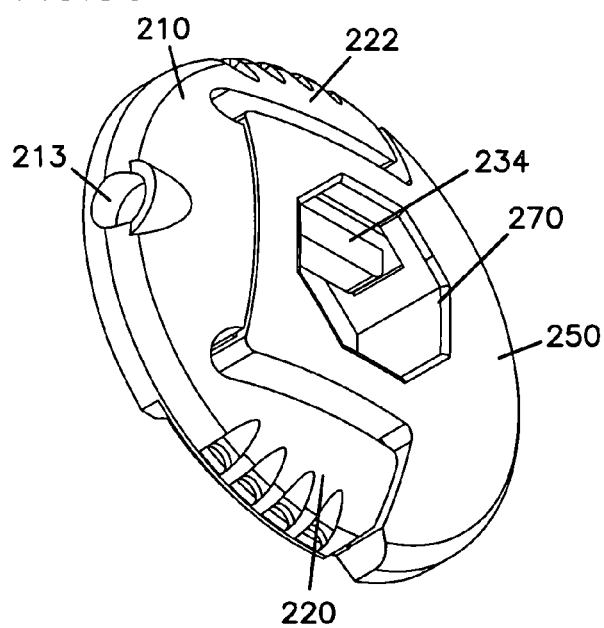
FIG. 36 is a top perspective view of the set of FIG. 21 in a locked position.
Figure 37:
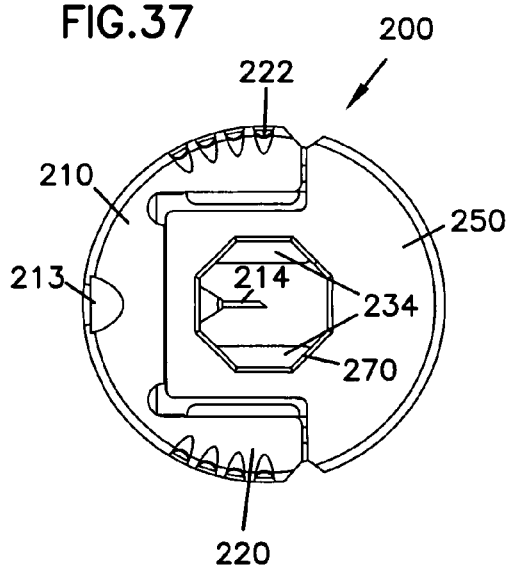
FIG. 37 is a top view of the set of FIG. 36.
Figure 38:
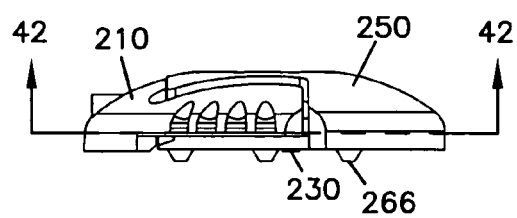
FIG. 38 is a side view of the set of FIG. 36.
Figure 43:
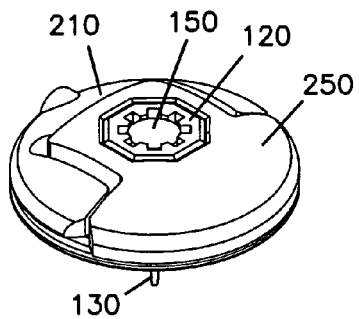
FIG. 43 is a perspective view of the site of FIG. 1 and the set of FIG. 21 coupled to one another.
Figure 44:
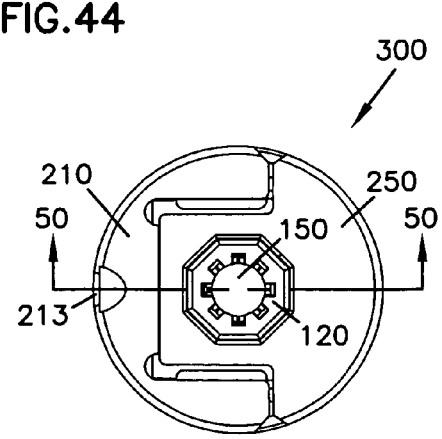
FIG. 44 is a top view of the site and set of FIG. 43.
Figure 45:
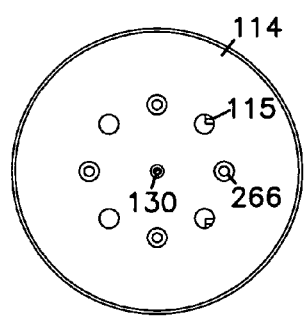
FIG. 45 is a bottom view of the site and set of FIG. 43.
Figure 46:
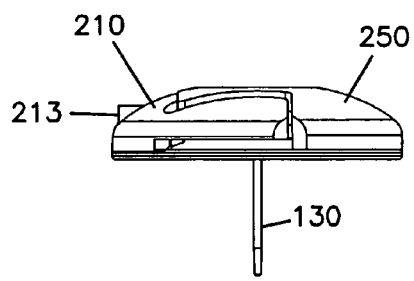
FIG. 46 is a side view of the site and set of FIG. 43.
Figure 47:
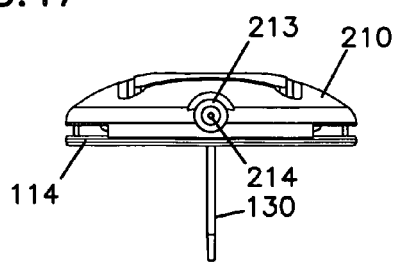
FIG. 47 is an end view of the site and set of FIG. 43.
Figure 48:
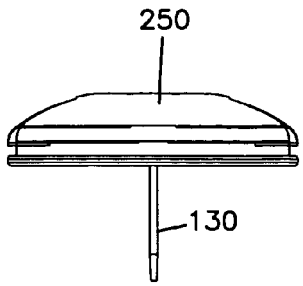
FIG. 48 is another end view of the site and set of FIG. 43.
Figure 49:
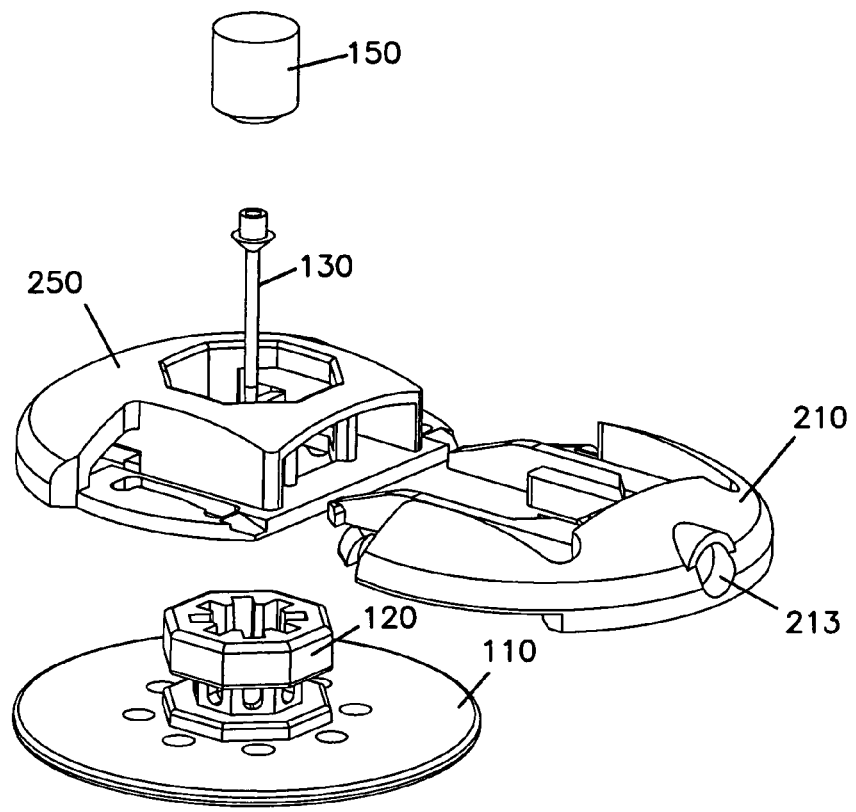
FIG. 49 is an exploded perspective view of the site and set of FIG. 43.

As illustrated by FIG. 35, in the unlocked position barbs 229 of inner arms 226 and 228 of the first member 210 extend through openings 264 and engage shoulders 271 of the second member 250 such that the first and second members 210 and 250 cannot be further separated.

Referring now to FIGS. 36-42, the first and second members 210 and 250 of the set 200 are shown in the locked position. To move the set 200 from the unlocked to the locked position, the first and second members 210 and 250 are slid towards one another, and outer arms 220 and 222 of the first member 210 are accepted into the openings 264 of the second member 250. Likewise, projections 230 on outer arms 220 and 222 slide along slots 268 of the second member 250. Further, surfaces 234 of the inner arms 226 and 228 partially extend into aperture 270, as described further below.

As illustrated by FIG. 42, in the locked position outer arms 220 and 222 extend through openings 264 and engage lips 272 of the second member 250. In addition, inner arms 226 and 228 of the first member 210 extend further into the second member 250. In this locked position, the engagement of the barbs 223 with the lips 272 resist allowing the first member 210 from being slid relative to the second member 250.

In order to slide the first member 210 away from the second member 250 from the locked position back to the unlocked position, the outer arms 220 and 222 are deflected inwardly toward one another by applying pressure on surfaces 221 until the barbs 223 clear the lips 272, thereby allowing the first member 210 to be slid with respect to the second member 250 back into the unlocked position as shown in FIGS. 21 and 32-35.

Preferably, slots 268 formed in the second member 250 include a cammed surface 269 so that projections 230 extending below the arms 220 of the first member 210 are biased towards a first end 267 of the slots 268 to thereby bias the first member 210 into the unlocked position. See FIGS. 40 and 41. In alternative embodiments, other features can be provided to bias the first member 210 into the unlocked position. For example, detents can be provided to engage barbs 229 as inner arms 226 and 228 of the first member 210 are moved towards the locked position to bias the first member 210 into the unlocked position. It can be preferable to bias the set 200 into the unlocked position so that the set 200 can be easily positioned onto and removed from the site 100, as described further below.

Referring now to FIGS. 43-50, as previously noted the site 100 and set 200 can be used together to form an infusion device 300 for delivery of a substance to a patient.

One method of use of the infusion device 300 is as follows. Initially, the site 100 is positioned on the skin of a patient with the cannula 130 being introduced into the subcutaneous layer of the skin. This can be accomplished, for example, using a needle (e.g., needle 130 shown in FIG. 6A) that is extended through the exposed closed end 154 of the diaphragm 150 and through the bore 142 of the cannula 130 and beyond the second end 134. The tapered portion 138 of the flange portion 136 of the cannula 130 can assist in directing the needle through into the bore 142 of the cannula 130. In this position, the needle can be used to introduce the cannula 130 of the site 100 into the skin of the patient. Further, once the cannula 130 is in position, the needle can be removed, leaving the cannula 130 in place in the subcutaneous layer of the skin. As the needle is removed, the closed end 154 of the diaphragm 150 reseals itself to retain the fluid-tight reservoir 158.

In a preferred embodiment, the site 100 of the infusion device 300 is placed in position on the skin of a patient using a device made in accordance with that disclosed in U.S. patent application Ser. No. 10/705,725, entitled "Device and Method for Insertion of a Cannula of an Infusion Device," and filed on Nov. 10, 2003, the entirety of which is hereby incorporated by reference. Other methods and devices for inserting the infusion device into the skin of the patient can also be used. For example, in an alternative embodiment the site 100 can be inserted manually using a needle. See needle 139 shown in FIG. 6A.

Once the site 100 has been positioned on the skin of a patient (with the cannula 130 having been introduced into the subcutaneous layer), the set 200 can be coupled to the site 100 as follows. With the set 200 in the unlocked position, the set 200 can be placed over the member 120 so that the central octagonal aperture 270 of the set 200 accepts the member 120 into the aperture 270. The set 200 is lowered onto the site 100 until the bottom surface 274 of the set 200 contacts the stand 114 of the site 100 and projections 266 of the second member 250 are accepted into the positional slots 115 of the stand 114 of the base 110.

In this position on the site 100, the first member 210 of the set 200 can be slid from the unlocked to the locked position. As the first member 210 is slid to the locked position, surfaces 234 of the inner arms 226 and 228 (see FIGS. 23, 36, and 37) are accepted by the groove 112 of the member 120 of the base 100, which locks the set 200 to the site 100 so that the set 200 resists any upward force tending to remove the set 200 from the site 100 when the set 200 is in the locked position. In addition, the shape of the member 120 of the site 100 and the central aperture 270 of the set 200, as well as projections 266 received in slots 115, orient the set 200 with respect to the site 100 and function to resist rotation of the set 200 with respect to the site 100 when the set 200 is in the locked position.

Figure 50:
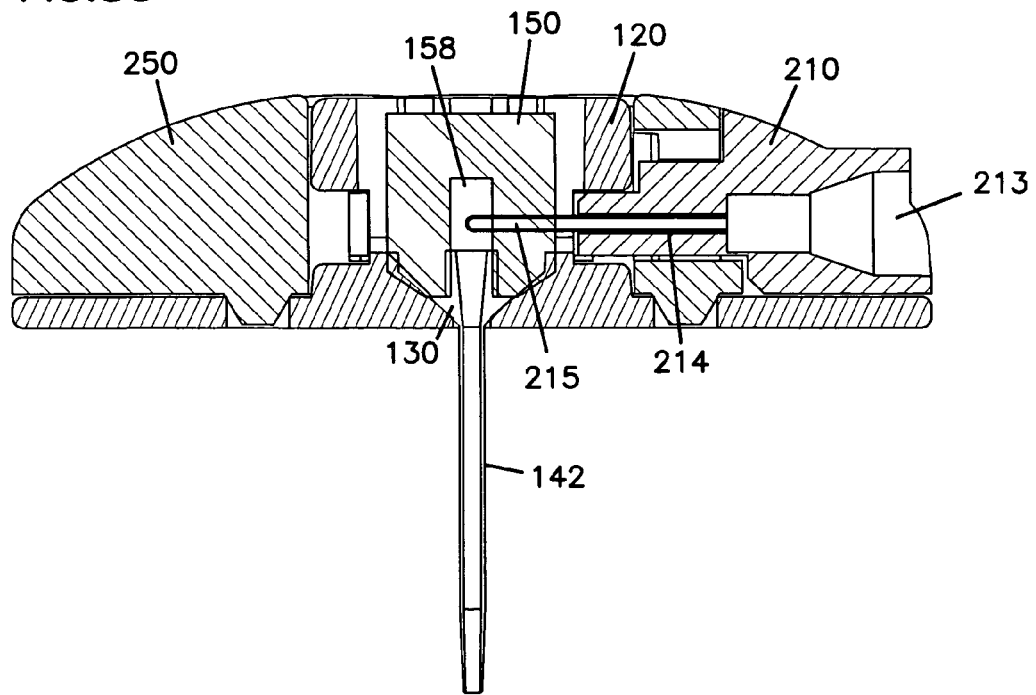
FIG. 50 is a cross-sectional view taken along line 50-50 of the site and set of FIG. 44.

In addition, as the first member 210 of the set 200 is moved from the unlocked to the locked position, the needle 214 is advanced through one of the eight apertures 123 formed in the member 120 and into the diaphragm 150 in the cavity 121. In the fully locked position as shown in FIG. 50, an end 215 of the needle 214 is positioned within the reservoir 158 of the diaphragm 150. In this position, the port 213 is fluidly coupled to the cavity 121 of the diaphragm 150 through the hollow needle 214, and the cavity 121 is in turn fluidly coupled to the skin of the patient through the bore 142 in the cannula 130. In this manner, a substance can be delivered to the port 213 of the set 200 (by, for example, a tube not shown in the figures), through the needle 214, into the reservoir 158, and into the subcutaneous layer of the skin of the patient by the cannula 130.

If the set 200 is not oriented as desired with respect to the site 100, or if the patient desires to remove the set 200 from the site 100, the set 200 can be moved from the locked to the unlocked position by forcing the outer arms 220 and 222 together and sliding the first member 210 away from the second member 250 to the unlocked position. This action removes the surfaces 234 from the groove 122, as well as the needle 214 from the reservoir 158. The diaphragm 150 reseals upon removal of the needle 214. The set 200 can then be removed from the site 100, leaving the site 100 in place on the skin of the patient. The set 200 can be replaced at another orientation or at a later time.

In the illustrated embodiment of the infusion device 300, the set 200 can be oriented in eight different positions with respect to the site 100. In alternative embodiments, the site 100 and set 200 can be configured to include fewer or more positions as desired. For example, in an alternative embodiment the member 120 of the site 100 and the aperture 270 of the set 200 can be formed in the shape of a square if four orientational positions are desired.

Figure 52:
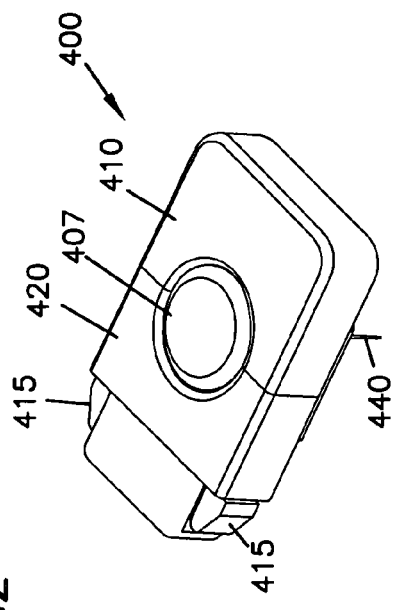
FIG. 52 is a perspective view of the infusion device of FIG. 51 in a locked position.
Figure 53:
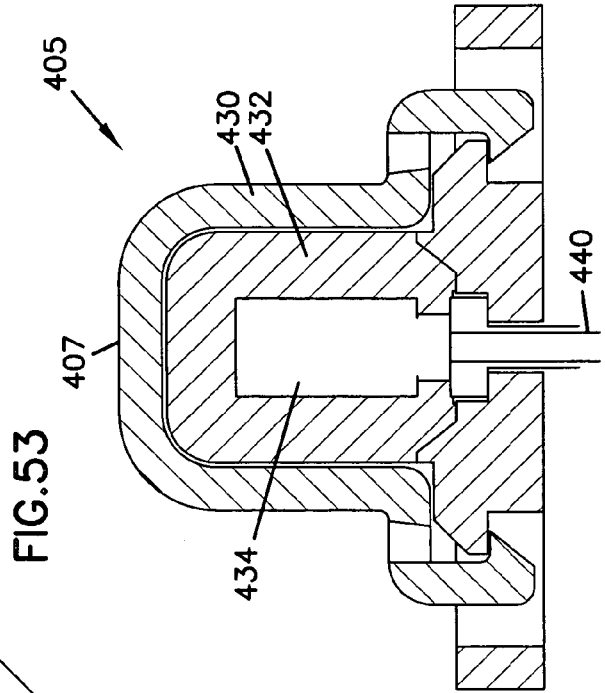
FIG. 53 is a cross-sectional view of the site of FIG. 51.
Figure 51:
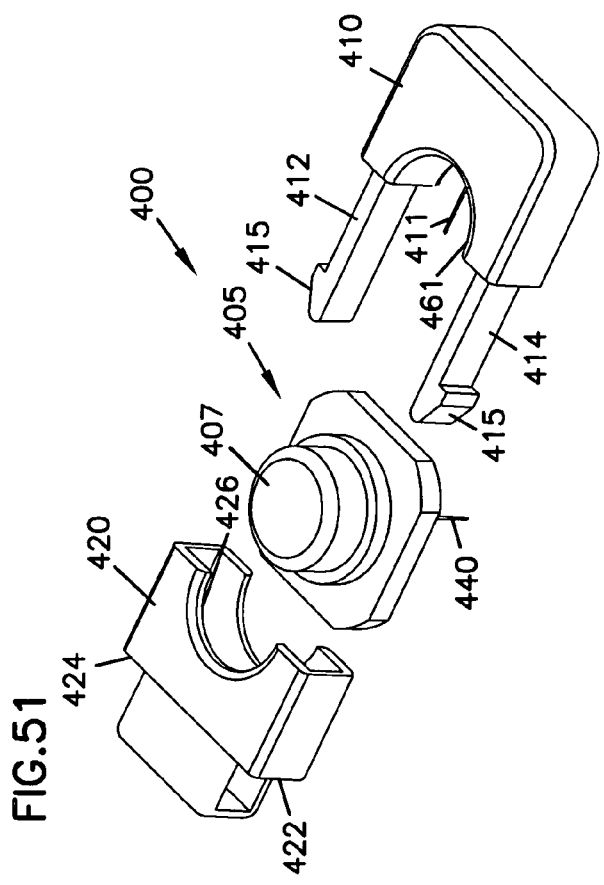
FIG. 51 is an exploded perspective view of another example embodiment of an infusion device including a site and set made in accordance with the present invention.
Figure 54:
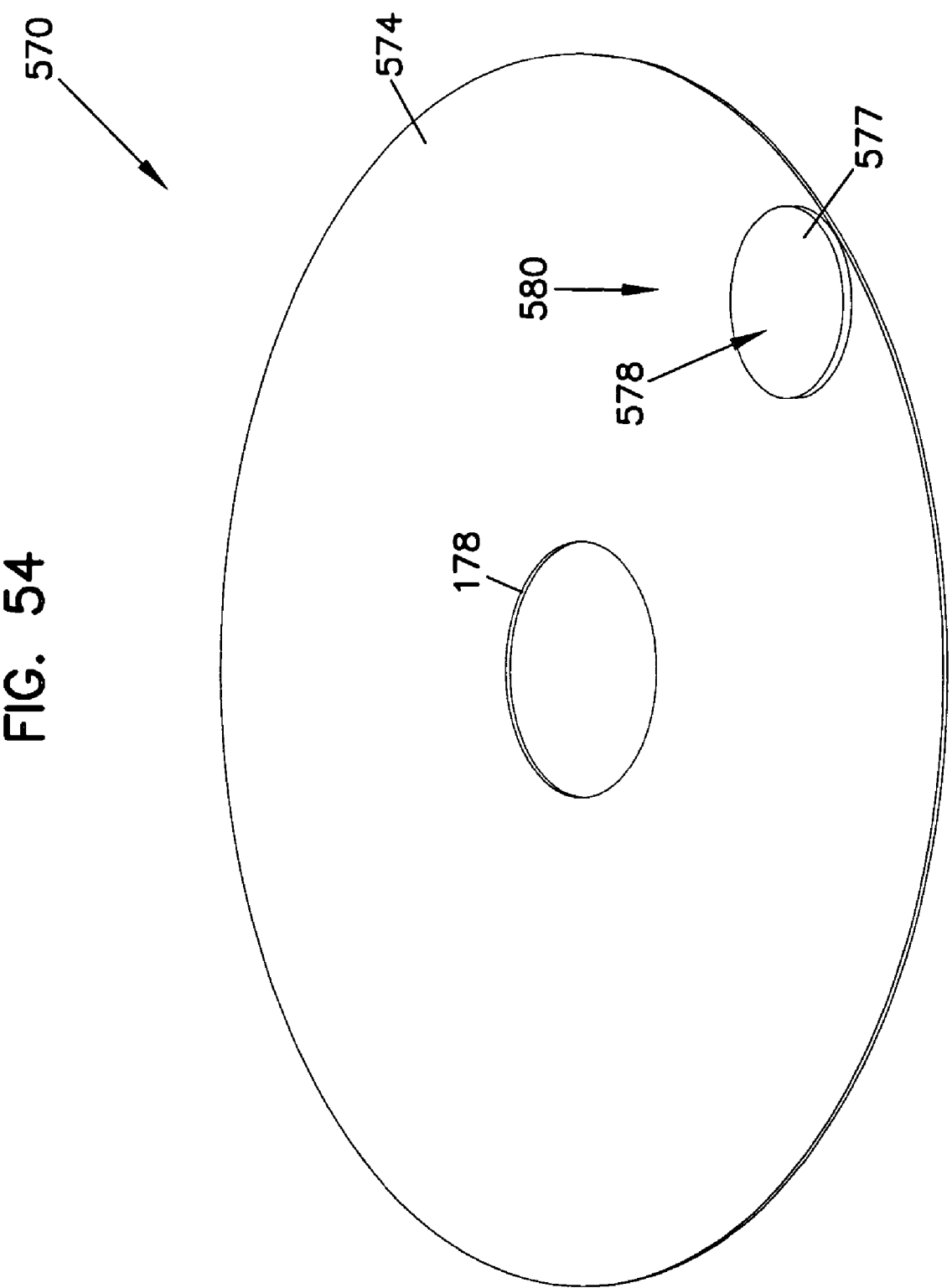
FIG. 54 is a bottom perspective view of another example embodiment of an adhesive portion including an example embodiment of a release feature made in accordance with the present invention.
Figure 55:
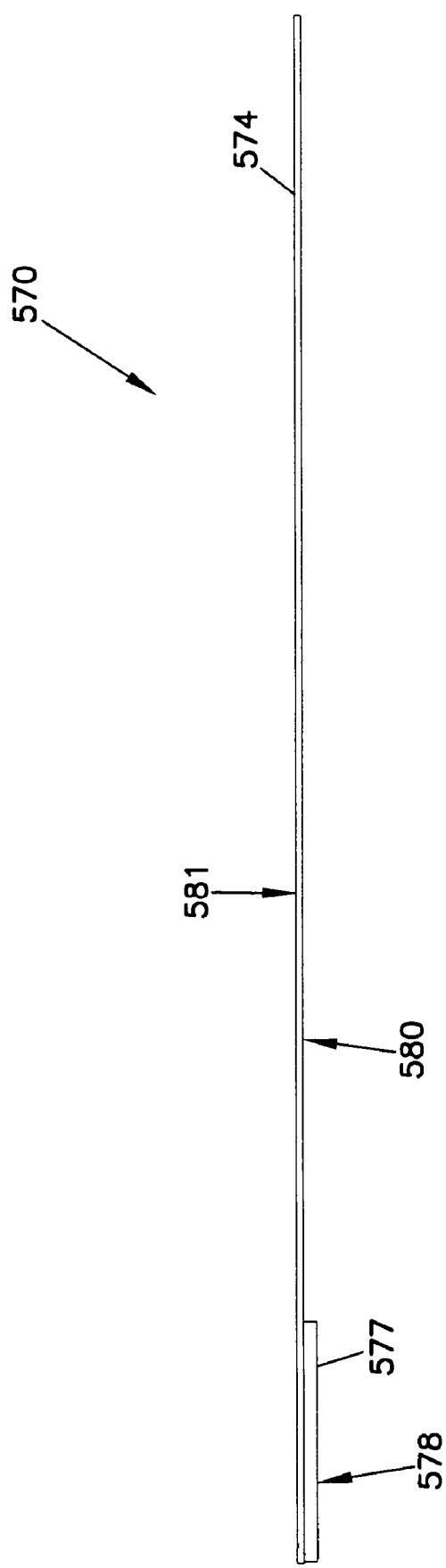
FIG. 55 is a side view of the adhesive portion of FIG. 54.

Referring now to FIGS. 51-53, another example infusion device 400 is shown in accordance with the present invention. The device 400 is similar to the example device 300 described above, except for the details noted below.

The infusion device 400 includes a site 405 with a central portion 407. The central portion 407 includes a pierceable outer shell 430 made of a material such as a plastic, and a softer inner diaphragm 432 surrounding the outer shell 430. An inner reservoir 434 of the central portion 407 is fluidly coupled to a cannula 440. See FIG. 53.

The infusion device 400 also includes a set with a first member 410 and a second member 420. The first member 410 includes a needle 411, and first and second arms 412 and 414 with barbs 415 on ends. The second member 420 includes shoulders 422 and 424. The first and second members 410 and 420 each form openings 461 and 462, respectively, that are sized to each receive a portion of the central portion 407 of the site 405.

The infusion device 400 can be used as follows. First, the site 405 is positioned on the skin of a patient so that the cannula 440 is introduced into the subcutaneous layer. Next, the first member 410 and second member 420 of the site are placed onto the site 405 so that openings 461 and 462 are positioned about the central portion 407, and the first and second members 410 and 420 are slid towards one another from the unlocked to the locked position. As the set is moved to the locked position, the needle 411 is introduced into the central portion 407 of the site 405, moving through the outer shell 430 and into the reservoir 434 to become fluidly coupled to the cannula 440. In addition, the arms 412 and 414 are accepted into the second member 420 until barbs 415 engage the shoulders 422 and 424 in the locked position, as shown in FIG. 52.

To move the set from the locked position back into the unlocked position, the barbs 415 are pressed inwardly toward one another until they clear the shoulders 422 and 424, and then the first member 410 is slid away from the second member 420, thereby removing the needle 411 from the central portion 407 of the site 405.

As preferably there is no specific structure provided with infusion device 400 for rotationally orienting the set with the site 405, the set can be oriented at an infinite number of rotational positions with respect to the site 405 as desired. Further, since the central portion 407 of the site and the openings 461 and 462 of the set are preferably circular in shape, the first and second members 410 and 420 of the site can be rotated relative to the site 405 without requiring that the set be completely removed from the site 405.

Referring now to FIGS. 54-61, an alternative embodiment is shown of an adhesive portion 570 that can be used to couple a site to the skin of a patient. Adhesive portion 570 includes a layer 574 similar to layers 174 and 174' described above. A bottom surface 580 of layer 574 includes an adhesive that couples layer 574 to the skin of the patient (see, for example, FIGS. 58-60 and accompanying description below).

Coupled to the bottom surface 580 of layer 574 is a release feature including a tab 577. Tab 577 is coupled to the bottom surface 580 of layer 574 using the adhesive of layer 574. In one embodiment, tab 577 includes adhesive on the surface of tab 577 that is coupled to layer 574 to further couple tab 577 to layer 574. An exposed surface 578 of tab 577 is substantially free of adhesive so that surface 578 does not adhere to the skin of a patient, as shown in FIGS. 58-60 described below.

Referring now to FIGS. 58-60, layer 574 is shown coupled to the skin 600 of a patient. Site 100 is coupled to a top surface 581 of layer 574. In FIG. 58, tab 577 is positioned between layer 574 and the skin 600 so that surface 578 of tab 577 contacts the skin 600 of the patient. Because surface 578 of tab 577 is substantially free of adhesive, surface 578 does not adhere to the skin 600, as described further below.

Referring now to FIG. 59, when a patient wants to remove site 100 and layer 574 from the skin 600, the patient lifts tab 577 away from the skin 600. As shown in FIG. 60, as the patient continues to pull on tab 577, layer 574 sheers away from the skin 600. The patient can continue to pull until layer 574 and accompanying site 100 are fully removed from the skin 600.

As illustrated by FIGS. 58-60, tab 577 assists the patient in removing layer 574 and accompanying site 100 from the skin 600. Because surface 578 of tab 577 does not adhere to the skin, the patient can grasp and pull the portion of layer 574 coupled to tab 577 to remove layer 574 from the skin.

In some embodiments, tab 577 extends beyond an outer periphery of layer 574, such as tab 177 shown in FIG. 20A. In other embodiments, tab 577 does not extend beyond the outer periphery of layer 574. In these embodiments, because tab 577 is located underneath layer 574 the location of tab 577 can be identified using visual and/or tactile means. For example, in one embodiment, layer 574 is semi-transparent, so that the patient can visually locate the position of tab 577 to remove layer 574. In other embodiments, top surface 581 of layer 574 can be marked (e.g., using a distinguishing color and/or mark) so that the patient can visually locate the tab 577. In other embodiments, tab 577 can be formed with a sufficient depth and/or rigidity so that the user can feel where tab 577 is located. In some embodiments, top surface 581 can be physically marked so that the user can feel the location of tab 577. Being able to locate the tab 577 using touch can be important if the site is located on an area of the body that does not allow the user to see layer 574 (e.g., if placed on the back of a patient).

In one embodiment, layer 574 is made of a polyurethane film such as a Tegaderm™ film manufactured by 3M™ or an IV300™ film manufactured by Smith & Nephew. In one embodiment, tab 577 is made of a woven tape such as a rayon woven tape having part number 1538L manufactured by 3M™. Other materials can be used.

In some embodiments, tab 577 has a diameter of between 1/16 and 3/16 of an inch. In one embodiment, the diameter of tab 577 is 2/16 of an inch. In other embodiments, tab 577 can be formed into other shapes such as an oval, square, or rectangle.

Figure 61:
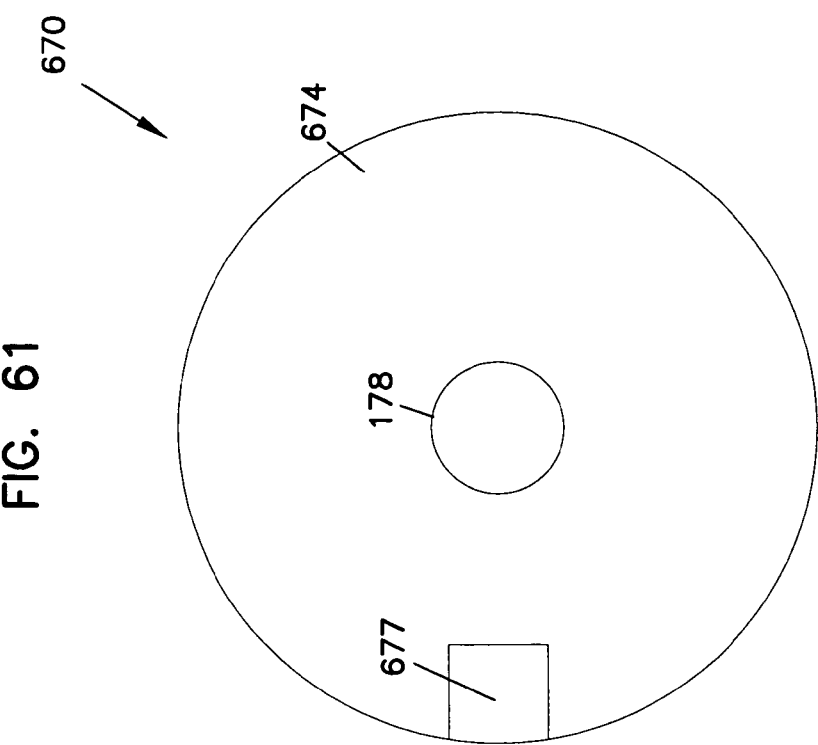
FIG. 61 is a bottom view of another example embodiment of an adhesive portion made in accordance with the present invention.
Figure 56:
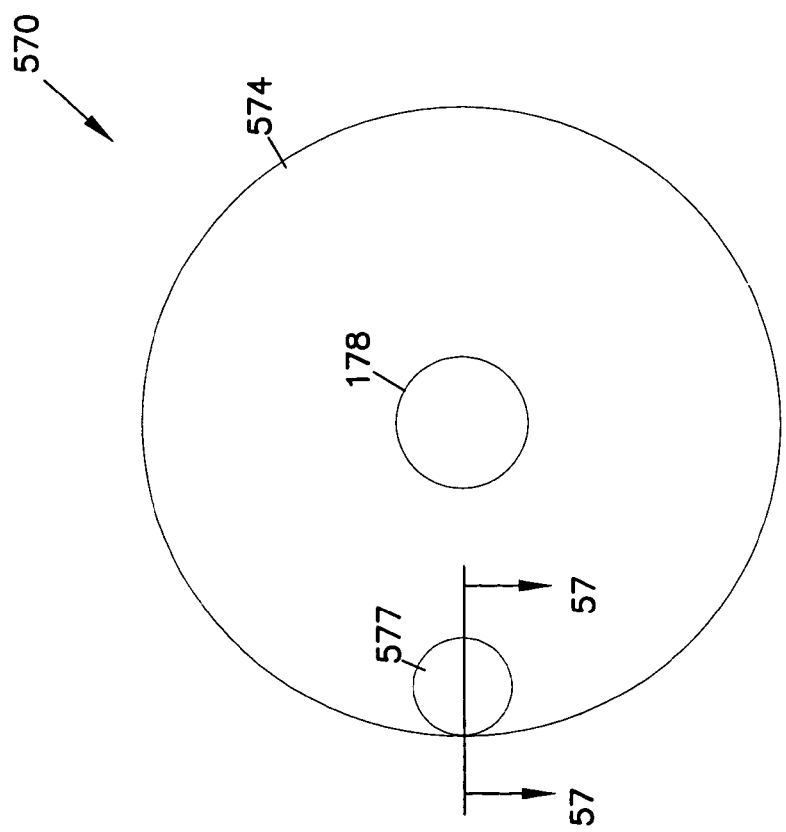
FIG. 56 is a top view of the adhesive portion of FIG. 54 with the release feature visible through the semi-transparent adhesive portion.
Figure 57:
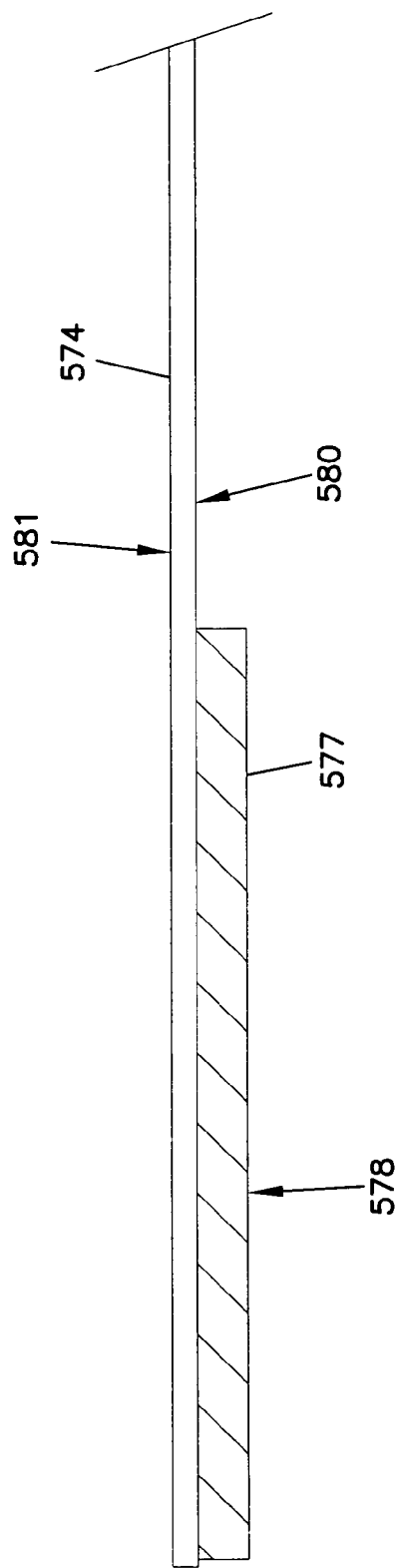
FIG. 57 is a cross-section view taken along lines 57-57 of a portion of the adhesive portion of FIG. 56.

FIG. 61 illustrates an alternative embodiment for an adhesive portion 670 including layer 674. Instead of including a separate tab, layer 674 has a release feature including a portion 677 of the surface of layer 674 that: (i) is substantially free of adhesive; and/or (ii) has had the adhesive thereon "voided" or otherwise inactivated or removed. Because portion 677 does not adhere to the skin, the patient can remove layer 674 from the skin by grasping portion 677 and pulling layer 674 away from the skin.

Portion 677 can be formed using various methods. In some methods, adhesive is not applied to portion 677 of layer 674. In other methods, adhesive that has been applied to the surface of layer 674 is removed for portion 677. In yet other embodiments, a powder or a similar media is applied at portion 677 to reduce the adhesive properties of the adhesive at portion 677.

Infusion devices made in accordance with the principles described herein can be advantageous for various reasons. For example, the set can be coupled in various selectable rotational orientations with respect to the site. In some embodiments, a plurality of orientations can be provided. This allows a patient to rotationally orient the set (and associated tube coupled to the set) as desired so that the tube can extend, for example, towards an infusion pump regardless of where the site is placed on the body of the patient.

In addition, the set and associated tube can be removed from the site multiple times while leaving the site on the skin. This can be desirable if the patient wants to reorient the set with respect to the site, or if the patient wants to remove the set from the site for a period of time, such as if the patient wishes to shower and then replace the set onto the site.

The engagement of the set with the site and sliding action of the set from the unlocked to locked position can also be advantageous in that a patient can preferably accomplish orientation and coupling of the set to the site using a single hand. This can be preferable, for example, if the site has been placed on a portion of the body of the patient that is not easily reached using two hands, or cannot easily be seen by the patient (e.g., if the site is placed on the back of the patient).

Further, the configuration of the set functions to protect the patient from inadvertent contact with the hollow needle (e.g., needles 214 and 411) used to pierce the diaphragm and deliver the substance to the site. For example, the outer arms 220 and 222 and the inner arms 226 and 228 of the first member 210 of the set 200 generally surround the needle 214 and function to reduce the chance that the patient will inadvertently contact the needle.

Also, the configuration of the diaphragm in the site can be preferable in that a single diaphragm can function to both allow introduction of the cannula of the site into the body using one needle, as well as coupling of the set with the site using a second needle. In addition, the diaphragm can preferably be held within the site through frictional engagement between the diaphragm and the site without requiring additional structure to retain the diaphragm in the site.

Although examples of infusion devices have been described herein, various modifications can be made to the devices. For example, as noted above the member 120 of the site 100 and the aperture 270 of the set 200 can be formed in a variety of shapes to allow the set 200 to be oriented in multiple positions with respect to the site 100. In addition, a retaining member can be fitted over the open top of the member 120 to further retain the diaphragm 150 in position in the cavity 121.

In another alternative embodiment, the second member 250 of the site 200 can be constructed to include a cover portion extending from the main body 260 so that when the set 200 is moved to the locked position the cover extends over the closed end 154 of the diaphragm 150 to reduce exposure of the set and site to outside contaminants.

The above specification, examples and data provide a complete description of the manufacture and of the invention. Since many embodiments of the invention can be made without departing from the spirit and scope of the invention, the invention resides in the claims hereinafter appended.

What is claimed is:

1. A subcutaneous infusion device, comprising:
   a site including a cannula extending from the site and configured to be introduced into a subcutaneous layer of skin of the patient;
   an adhesive portion including a first surface coupled to the site and a second surface including an adhesive configured to be coupled to the skin of the patient; and
   a release feature coupled to the adhesive portion, wherein the release feature assists the patient in removing the adhesive portion from the skin, and wherein the release feature is positioned between the adhesive portion and the skin and is configured to contact the skin,
   wherein the adhesive portion includes a visual indicator positioned on the first surface of the adhesive portion to assist the patient in locating the release feature.

2. The device of claim 1, wherein the release feature is a tab.

3. The device of claim 2, wherein the tab extends beyond an outer periphery of the adhesive portion.

4. The device of claim 1, wherein the release feature is a portion of the second surface of the adhesive portion whereat the adhesive has been voided.

5. A subcutaneous infusion device, comprising:
   a site including a cannula extending from the site and configured to be introduced into a subcutaneous layer of skin of the patient;
   an adhesive portion including a first surface coupled to the site and a second surface including an adhesive configured to be coupled to the skin of the patient; and
   a region coupled to the adhesive portion, wherein the region defines an exposed surface that is substantially free of adhesive so that, when the adhesive portion is applied to the skin of the patient, the region is positioned between the adhesive portion and the skin and the region contacts but does not adhere to the skin, and wherein the patient can grasp the region to remove the adhesive portion from the skin,
   wherein the adhesive portion includes a visual indicator positioned on the first surface of the adhesive portion to assist the patient in locating the release feature.

6. The device of claim 5, wherein the region is a tab.

7. The device of claim 5, wherein the adhesive portion is at least partially semi-transparent so that the patient can visually locate the region through the adhesive portion.

8. The device of claim 5, wherein the region is formed of sufficient rigidity so that the patient can feel the region through the adhesive portion.

* * * * *